United States Patent
Brendel et al.

(10) Patent No.: US 8,468,664 B2
(45) Date of Patent: Jun. 25, 2013

(54) PROCESS FOR MANUFACTURING EMI FILTERS UTILIZING COUNTER-BORED CAPACITORS TO FACILITATE SOLDER RE-FLOW

(75) Inventors: Richard L. Brendel, Carson City, NV (US); Jason Woods, Carson City, NV (US); Jose Luis Lorente-Adame, Tijuana (MX); Robert A. Stevenson, Canyon Country, CA (US); John Roberts, Carson City, NV (US); Buehl E. Truex, Glendora, CA (US)

(73) Assignee: Greatbatch Ltd., Clarence, NY (US)

( * ) Notice: Subject to any disclaimer, the term of this patent is extended or adjusted under 35 U.S.C. 154(b) by 601 days.

(21) Appl. No.: 12/437,345

(22) Filed: May 7, 2009

(65) Prior Publication Data
US 2009/0288280 A1 Nov. 26, 2009

Related U.S. Application Data

(60) Provisional application No. 61/055,305, filed on May 22, 2008.

(51) Int. Cl.
*H01G 7/00* (2006.01)
(52) U.S. Cl.
USPC ........ 29/25.42; 29/25.41; 29/592.1; 361/302; 607/5
(58) Field of Classification Search
USPC .......... 29/25.35–25.42, 830–831, 832, 592.1; 361/302, 307, 306.2; 607/5; 333/182–185
See application file for complete search history.

(56) References Cited

U.S. PATENT DOCUMENTS

| | | | |
|---|---|---|---|
| 2,756,375 A * | 7/1956 | Peck | 361/302 |
| 3,578,895 A | 5/1971 | Caires | |
| 4,424,551 A | 1/1984 | Stevenson et al. | |
| 4,741,710 A | 5/1988 | Hogan et al. | |
| 5,333,095 A | 7/1994 | Stevenson et al. | |
| 5,825,608 A | 10/1998 | Duva et al. | |
| 5,905,627 A | 5/1999 | Brendel et al. | |
| 6,055,455 A | 4/2000 | O'Phelan et al. | |
| 6,118,647 A | 9/2000 | Okinaka et al. | |
| 6,275,269 B1 | 8/2001 | Nguyen et al. | |
| 6,275,369 B1 | 8/2001 | Stevenson et al. | |
| 6,349,025 B1 | 2/2002 | Fraley et al. | |
| 6,456,481 B1 | 9/2002 | Stevenson | |
| 6,459,935 B1 | 10/2002 | Piersma | |
| 6,519,133 B1 | 2/2003 | Eck et al. | |
| 6,566,978 B2 | 5/2003 | Stevenson et al. | |
| 6,621,682 B1 | 9/2003 | Takakuwa et al. | |
| 6,643,903 B2 * | 11/2003 | Stevenson et al. | 29/25.41 |
| 6,660,116 B2 | 12/2003 | Wolf et al. | |
| 6,765,779 B2 * | 7/2004 | Stevenson et al. | 361/302 |

(Continued)

FOREIGN PATENT DOCUMENTS

| | | |
|---|---|---|
| JP | 02260902 | 10/1990 |
| JP | 2010150076 | 7/2010 |

*Primary Examiner* — Minh Trinh
(74) *Attorney, Agent, or Firm* — Michael F. Scalise

(57) ABSTRACT

An EMI filtered terminal assembly including at least one conductive terminal pin, a feedthrough capacitor, and a counter-bore associated with a passageway through the capacitor is described. Preferably, the feedthrough capacitor having counter-drilled or counter-bored holes on its top side is first bonded to a hermetic insulator. The counter-drilled or counter-bore holes in the capacitor provide greater volume for the electro-mechanical attachment between the capacitor and the terminal pin or lead wire, permitting robotic dispensing of, for example, thermal-setting conductive adhesive.

30 Claims, 14 Drawing Sheets

U.S. PATENT DOCUMENTS

| | | | |
|---|---|---|---|
| 6,765,780 B2 | 7/2004 | Brendel et al. | |
| 6,888,715 B2 * | 5/2005 | Stevenson et al. | 361/302 |
| 6,985,347 B2 * | 1/2006 | Stevenson et al. | 361/302 |
| 6,999,818 B2 | 2/2006 | Stevenson et al. | |
| 7,012,192 B2 | 3/2006 | Stevenson et al. | |
| 7,035,076 B1 * | 4/2006 | Stevenson | 361/302 |
| 7,038,900 B2 | 5/2006 | Stevenson et al. | |
| 7,054,136 B2 | 5/2006 | Ritter et al. | |
| 7,113,387 B2 | 9/2006 | Stevenson et al. | |
| 7,145,076 B2 | 12/2006 | Knappen et al. | |
| 7,199,995 B2 | 4/2007 | Stevenson et al. | |
| 7,295,421 B2 | 11/2007 | Mihara et al. | |
| 7,310,216 B2 | 12/2007 | Stevenson et al. | |
| 7,327,553 B2 | 2/2008 | Brendel | |
| 7,408,762 B2 | 8/2008 | Taller et al. | |
| 7,489,495 B2 * | 2/2009 | Stevenson | 361/302 |
| 7,493,167 B2 | 2/2009 | Hussein et al. | |
| 7,535,693 B2 | 5/2009 | Stevenson et al. | |
| 7,539,004 B2 | 5/2009 | Iyer et al. | |
| 7,765,005 B2 | 7/2010 | Stevenson | |
| 2001/0050837 A1 | 12/2001 | Stevenson et al. | |
| 2002/0017700 A1 | 2/2002 | Mori et al. | |
| 2002/0166618 A1 | 11/2002 | Wolf et al. | |
| 2005/0247475 A1 | 11/2005 | Stevenson et al. | |
| 2007/0035910 A1 | 2/2007 | Stevenson | |
| 2007/0217121 A1 | 9/2007 | Fu et al. | |
| 2007/0279833 A1 | 12/2007 | Iyer et al. | |
| 2008/0140148 A1 | 6/2008 | Rogier | |
| 2008/0294220 A1 | 11/2008 | Stevenson et al. | |
| 2009/0034152 A1 | 2/2009 | Aoki et al. | |
| 2009/0059468 A1 | 3/2009 | Iyer | |
| 2009/0079517 A1 | 3/2009 | Iyer | |
| 2009/0079518 A1 | 3/2009 | Iyer | |
| 2009/0079519 A1 | 3/2009 | Iyer | |
| 2009/0080140 A1 | 3/2009 | Iyer et al. | |
| 2009/0128986 A1 | 5/2009 | Brendel et al. | |
| 2010/0023086 A1 | 1/2010 | Lim | |
| 2010/0134951 A1 | 6/2010 | Brendel et al. | |

* cited by examiner

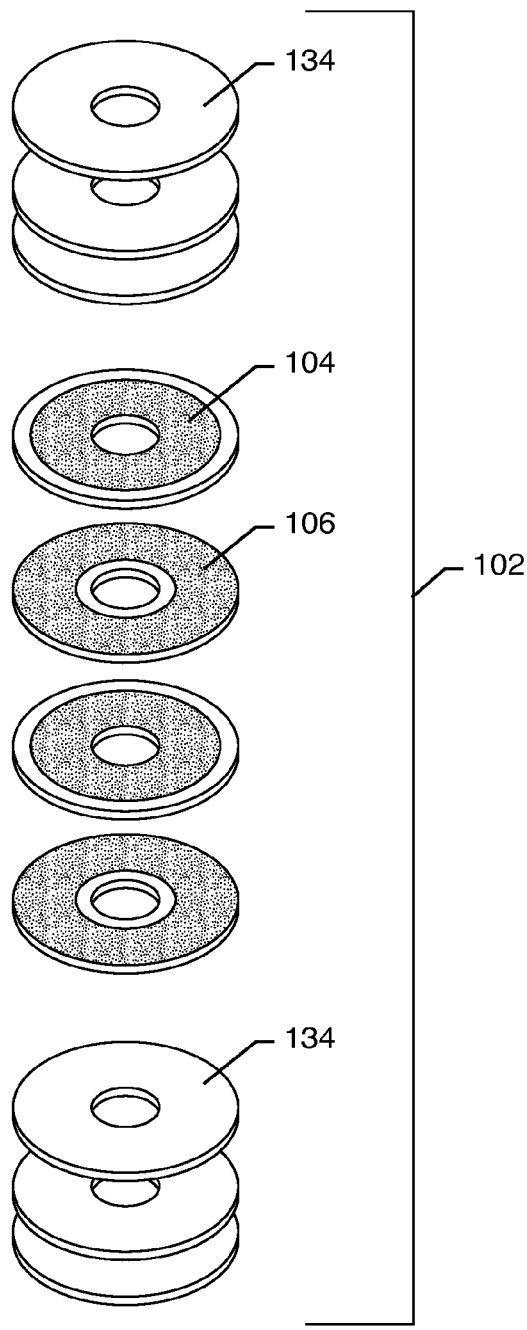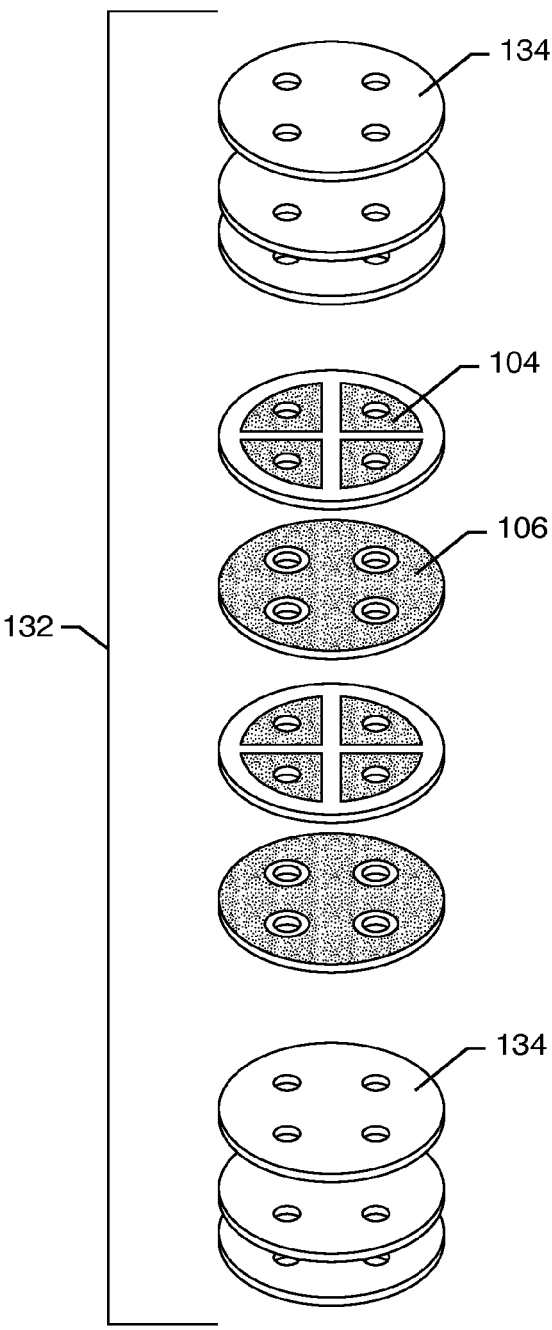
FIG. 8
PRIOR ART
FIG. 9
PRIOR ART

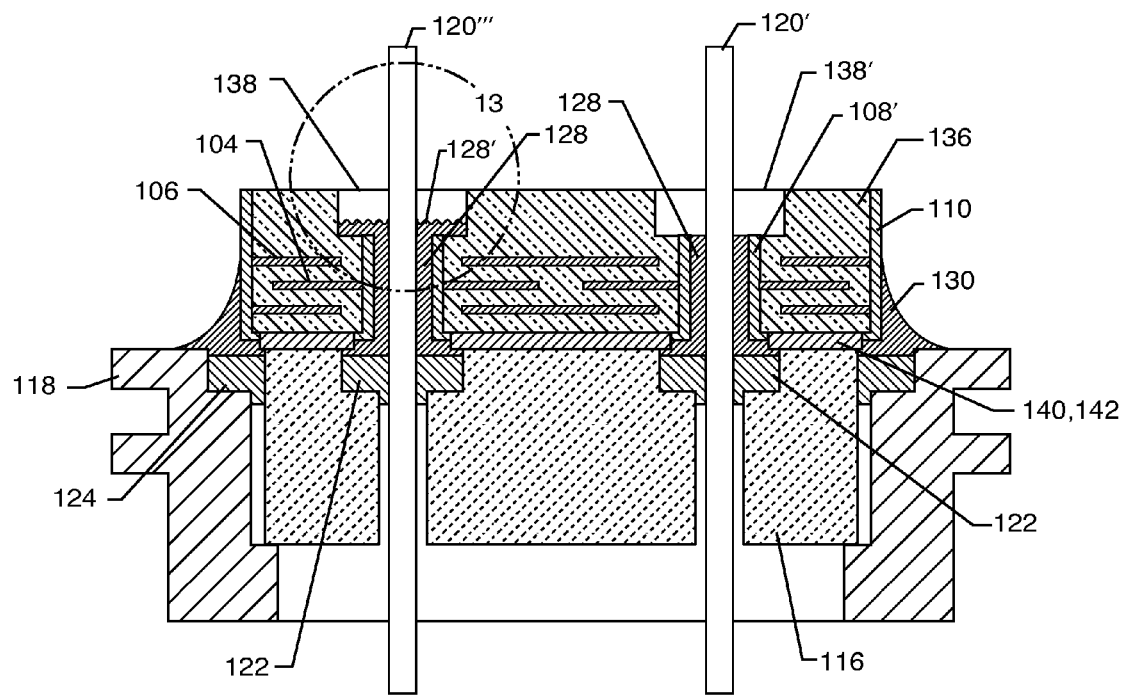
FIG. 12
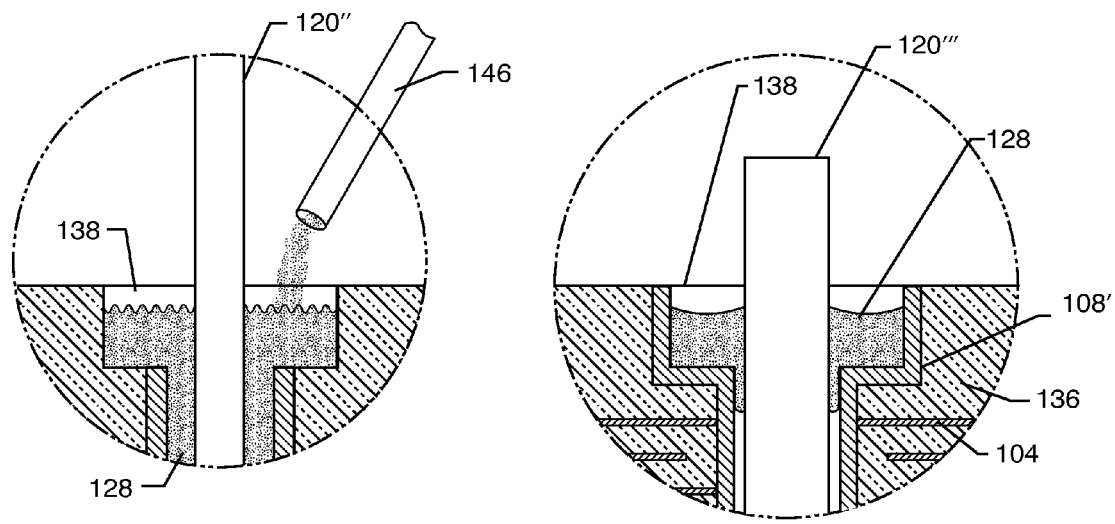
FIG. 13
FIG. 14

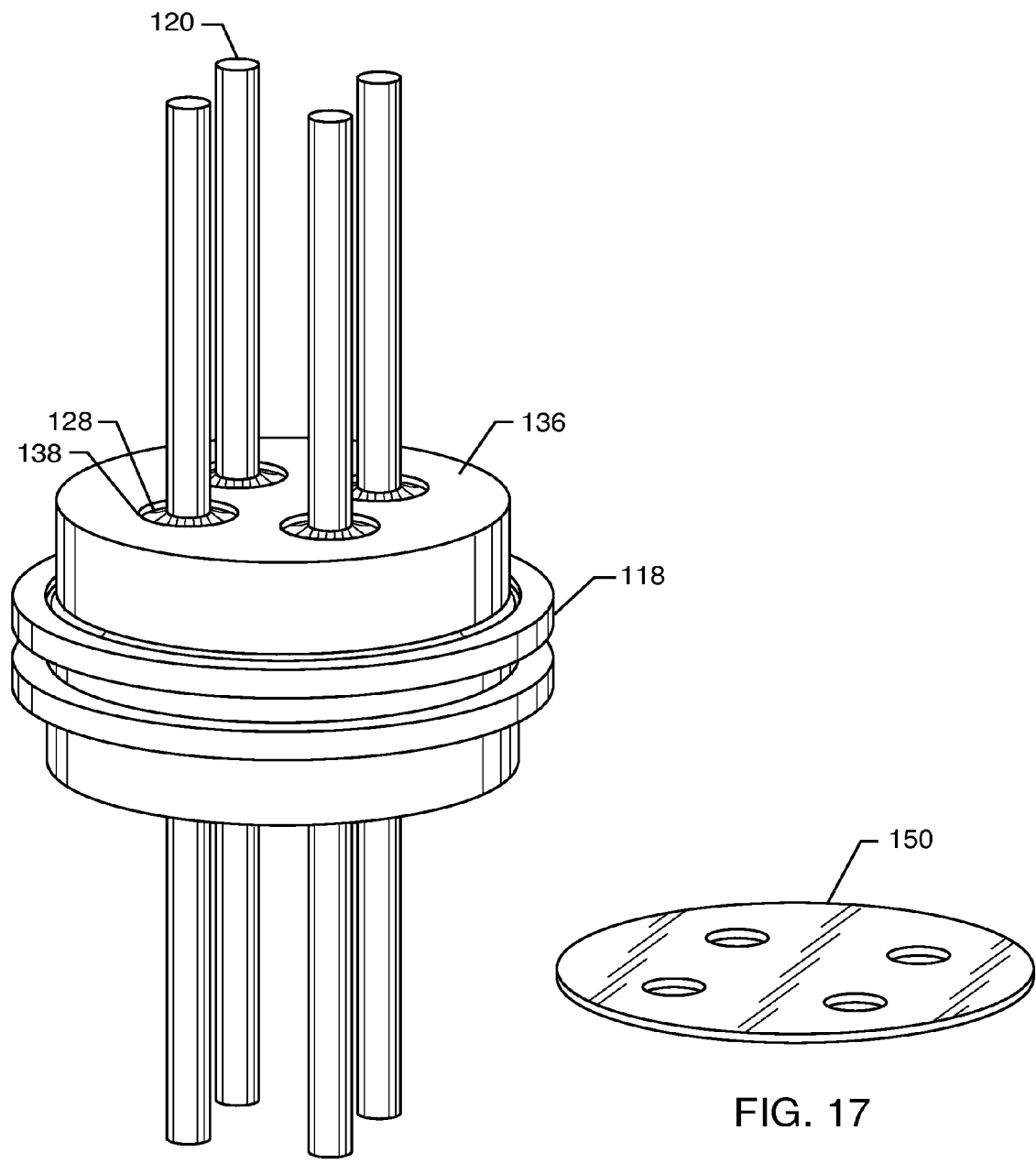

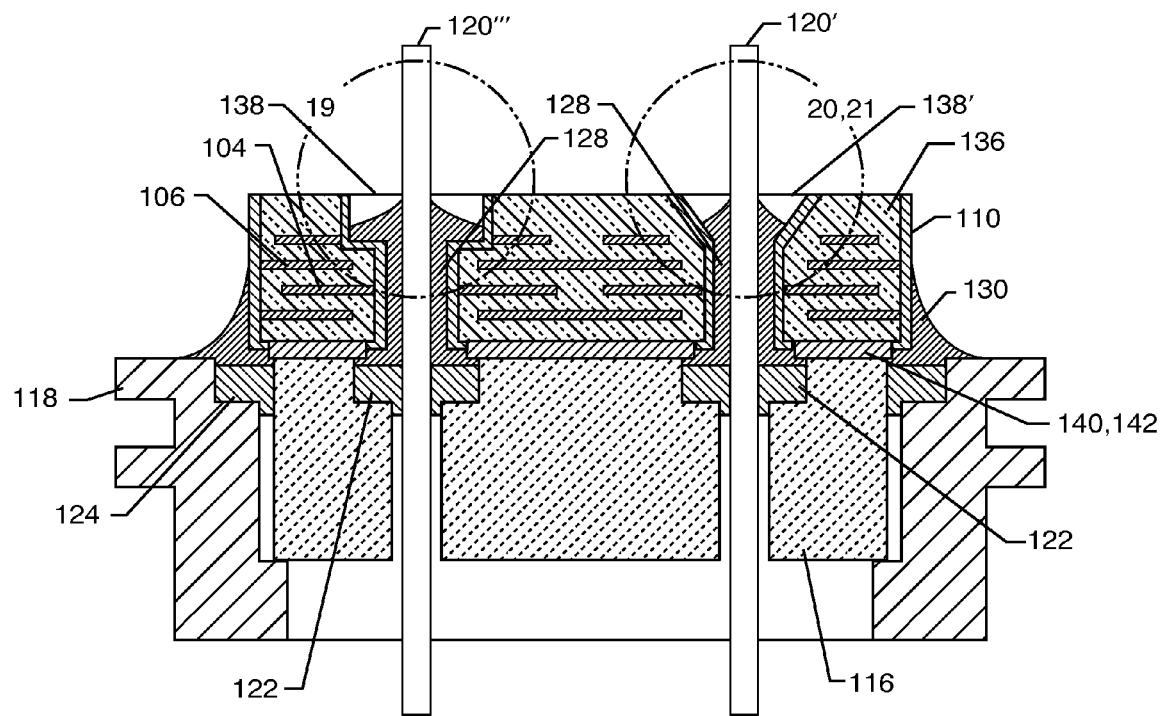
FIG. 18
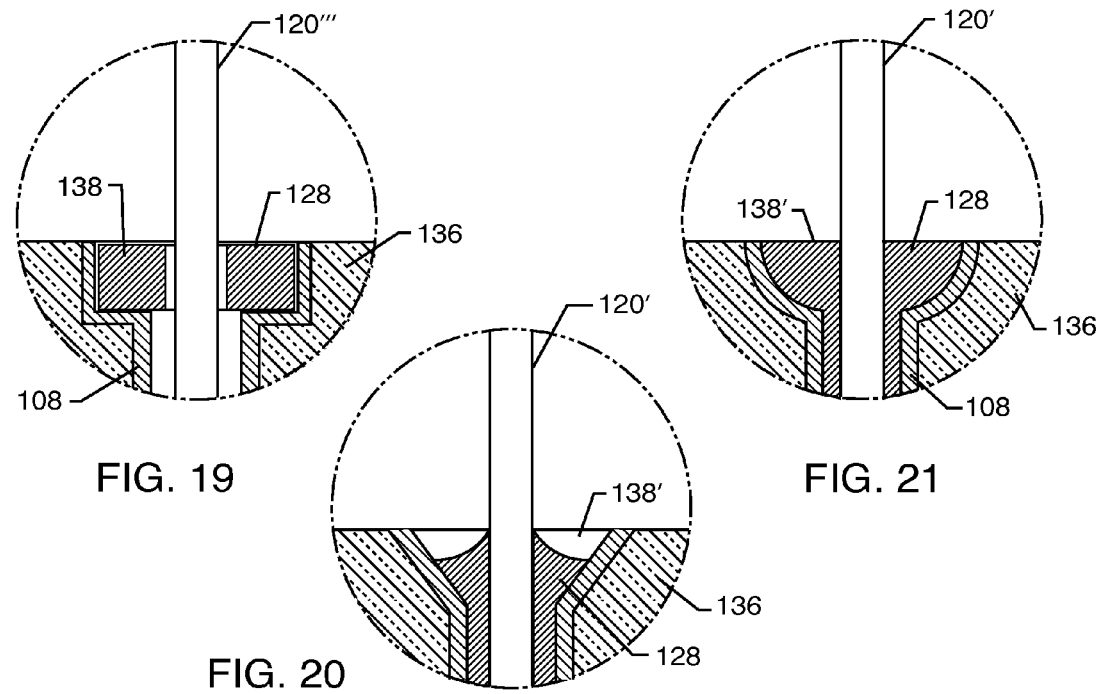
FIG. 19
FIG. 20
FIG. 21

PROCESS FOR MANUFACTURING EMI FILTERS UTILIZING COUNTER-BORED CAPACITORS TO FACILITATE SOLDER RE-FLOW

BACKGROUND OF THE INVENTION

This invention relates generally to EMI filter terminal subassemblies and related methods of construction, particularly of the type used in active implantable medical devices (AIMDs) such as cardiac pacemakers, implantable defibrillators, cochlear implants, neurostimulators, active drug pumps and the like, which are designed to decouple and shield undesirable electromagnetic interference (EMI) signals from an associated device. More particularly, the present invention relates to an improved EMI filter capacitor that includes various types of counter-drills, counter-sinks or counter-bores for convenient attachment of the feedthrough capacitor to the associated lead wires. The counter-drills, counter-sinks and counter-bores form a convenient well for placement of a thermal setting conductive adhesive, solder, braze material or the like.

Feedthrough terminal assemblies are generally well known for connecting electrical signals through the housing or case of an electronic instrument. For example, in implantable medical devices, the terminal pin assembly comprises one or more conductive terminal pins supported by an insulator structure for a feedthrough passage from the exterior (body fluid side) to the interior of the medical device. Many different insulator structures and related mounting methods are known for use in medical devices wherein the insulator structure provides a hermetic seal to prevent entry of body fluids into the housing of the medical device. In a cardiac pacemaker, for example, the feedthrough terminal pins are typically connected to one or more lead wires within the case to conduct pacing pulses to cardiac tissue and/or detect or sense cardiac rhythms. However, the lead wires can also undesirably act as an antenna and thus tend to collect stray electromagnetic interference (EMI) signals for transmission into the interior of the medical device. Studies conducted by the United States Food and Drug Administration (FDA), Mount Sinai Medical Center and other researchers have demonstrated that stray EMI, such as RF signals produced by cellular telephones, can seriously disrupt the proper operation of the pacemaker. It has been well documented that pacemaker inhibition, asynchronous pacing and misbeats can all occur. All of these situations can be dangerous or even life threatening for a pacemaker-dependent patient.

In prior art devices, such as those as shown in U.S. Pat. Nos. 5,333,095 and 4,424,551 (the contents of which are incorporated herein), the hermetic terminal pin subassembly has been combined in various ways with a ceramic feedthrough capacitor filter to decouple EMI signals to the equipotential housing of the medical device. As described in U.S. Pat. No. 6,999,818 (the contents of which are incorporated herein), the feedthrough capacitor can also be combined with inductor elements thereby forming what is known in the art as a multi-element low pass filter.

In general, the ceramic feedthrough capacitor, which has one or more passages or feedthrough holes, is connected to the hermetic terminal of the implantable medical device in a variety of ways. In order for the EMI filtered feedthrough capacitor to properly operate, a low impedance and low resistance electrical connection must be made between the capacitor ground electrode plate stack, and the metallic ferrule of the hermetic seal, which in turn mechanically and electrically connects to the overall conductive housing of the implantable medical device. For example, in a cardiac pacemaker, the hermetic terminal assembly consists of a conductive ferrule generally made of titanium which is laser welded to the overall titanium housing of the implantable medical device. This not only provides a hermetic seal, but also makes the ferrule of the hermetic terminal a continuous part of the overall electromagnetic shield that protects the electronics of the implantable medical device from EMI. The ceramic feedthrough capacitor is in turn, electrically and mechanically bonded to the ferrule of said hermetic terminal. Prior art feedthrough capacitors have two plate sets. There is no real polarity associated with a monolithic ceramic capacitor dielectric. However, for the purposes herein, one of the plate stacks is known as the active plate stack, which will be connected to the feedthrough lead wires and the second electrode plate stack will be known as the ground electrode plate stack, which really isn't connected to a ground, but is connected to the overall electromagnetic shield of the active implantable medical device. In other words, this is a method of shield grounding rather than earth grounding.

In the past, and in particular as described in U.S. Pat. Nos. 5,333,095 and 4,424,551, the connection between the feedthrough capacitor and the ferrule is typically performed using a thermal-setting conductive adhesive. One such material is a silver flake loaded conductive polyimide. The connection between the lead wires of the hermetic terminal and the passages or feedthrough holes of the ceramic feedthrough capacitor are typically made with solder, a thermal-setting conductive adhesive, a braze material or the like. The perimeter or diameter of the feedthrough capacitor is typically where its ground electrodes are connected (reference U.S. Pat. No. 5,333,095). Methods of holding the thermal-setting conductive material in place are well described by the prior art, in particular by U.S. Pat. No. 6,643,903 (the contents of which are incorporated herein) which describes a capture flange for convenient dispensing of materials. It is also described by U.S. Pat. No. 6,275,269 (the contents of which are also incorporated herein). Various methods of providing for leak detection are also provided as described in U.S. Pat. No. 6,566,978 (the contents of which are incorporated herein). However, the methodology to make a proper electrical connection between the lead wires and the feedthrough capacitor holes remains problematic.

Prior art feedthrough capacitors generally have a metallization or termination surface around their outside diameter or outside perimeter. This places all of the ground electrode plates in parallel and also provides for a convenient place for attachment of solder or thermal-setting conductive adhesives or the like. In a similar fashion, the inside diameter or feedthrough holes also have an inside diameter metallization surface which puts the active electrode plate set together in parallel. Various methods are known in prior art to make an electrical contact between the feedthrough lead wire and this inside diameter metallization which in turn contacts all of the electrode plates of the active electrode plate set. Application of the prior art metallization (also known as termination) on the capacitor outside diameter and also into all of the capacitor feedthrough holes is a time consuming and costly process. For a typical quadpolar ceramic feedthrough capacitor, application of the termination usually involves placing the capacitor on a mandrel and then rolling its outside diameter through a bed of a liquid silver-bearing glass frit. This glass frit is fired in place thereby conductively coupling all of the ground electrode plates in parallel. Then a vacuum pull process is used to pull metallization or termination material consisting of the same silver or palladium silver glass frit through the ID holes. This is followed by another high temperature glass firing operation. These operations are then followed by lapping or clean up operations to be sure that for small diameter feedthrough capacitors that there is no metallization left on the top or bottom surfaces that could lead to shorting out of the device. Electroplating is an alternative process to accomplish the above. While these processes tend to be very reliable, they are very expensive and time consuming.

One such methodology is described in U.S. Pat. No. 4,424,551. However, the process of injecting a material through repeated centrifuge steps and then repeated microblast cleaning steps is very time consuming, costly and tends to result in low process yields. A superior method of mounting the ceramic feedthrough capacitor is described in U.S. Pat. No. 5,333,095 wherein the capacitor is surface mounted. This has great advantages in that the ceramic capacitor itself is not subjected to undue mechanical or thermal stresses during laser weld installation of the hermetic seal subassembly and to the overall housing of the AIMD. It is relatively easy to make the perimeter or outside diameter ground attachment to the ferrule. However, for a capacitor with a flat surface with lead wires extending through its through-holes, it is problematic to make a reliable electrical connection. This is because solders, thermal-setting conductive polymers, brazes and the like tend to sit up on top of the capacitor. During re-flow operations, at high temperature these materials tend to migrate into undesirable positions. Sometimes the materials will migrate together and even short out one lead to another.

Accordingly, there is a need for improved structure methods and for making connections between a feedthrough capacitor and its associated lead wires which overcome the aforementioned difficulties. The present invention solves all the aforementioned problems and facilitates manufacturing.

SUMMARY OF THE INVENTION

EMI filtered terminal assemblies constructed in accordance with the present invention comprise, generally, at least one conductive terminal pin, a filter capacitor, which in the case of a feedthrough filtered capacitor has a passageway through which one or more terminal pins extend, and one or more wells comprising counter-drills, counter-sinks or counter-bores, which are associated with said passageway and lead wire.

As used herein, the terms "counter-drills," "counter-sinks," and "counter-bores" are used interchangeably, all of which are known as "wells."

More particularly, the present invention involves a process for manufacturing an electromagnetic interference (EMI) filter for use in an active implantable medical device (AIMD).

The novel manufacturing process of the present invention comprises the steps of (1) providing a capacitor comprised of a dielectric material having active and ground electrode plates therein and at least one through hole; (2) forming a well in a surface of the capacitor at one end of the through hole; (3) inserting a pin or a lead wire at least partially into the through hole; (4) placing an electrically conductive material in the well, wherein the electrically conductive material comprises a liquid or semi-liquid material during at least some portion of the manufacturing process; and (5) utilizing the electrically conductive material to conductively couple the pin or the lead wire to one of the active or ground electrode plates. In most preferred embodiments shown herein, the novel manufacturing process further includes the step of utilizing an electrically conductive material to attach the pin or the lead wire to the capacitor.

A feedthrough capacitor is mounted to a hermetic seal and subassembly in accordance with one or more prior art methods as described in, for example, U.S. Pat. Nos. 4,424,551 and 5,333,095. The feedthrough capacitor has first and second sets of electrode plates also known as the ground electrode plate set and the active electrode plate set. As previously described, a metallization or termination surface is placed around the outside diameter (or perimeter) of the feedthrough capacitor and also around the inside diameter of each of the feedthrough holes. These termination surfaces connect the ground electrode plates and the active electrode plates in parallel respectively. The terminal pin(s) extend through the passageway(s) of the capacitor in conductive relation with the active set of electrode plates. In a typical implantable electronic device application like a cardiac pacemaker, there is a hermetic insulator supported by a conductive substrate (usually a titanium ferrule) through which the terminal pin passes in non-conductive relation. The capacitor may be bonded onto or into this insulator or separated from the insulator thereby forming a small air gap depending on the assembly method used. The outside diameter or perimeter of the capacitor is generally installed in conductive relation with the conductive substrate or ferrule so that the feedthrough capacitor is properly grounded. Alternative arrangements are shown in U.S. Pat. Nos. 5,905,627 and 7,199,995.

In a preferred embodiment, a feedthrough capacitor having counter-drilled holes on its top side is first bonded to the hermetic insulator. Then attachment is made to the lead wires through a variety of methods including soldering, placement of a thermal-setting conductive adhesive, braze material or the like. Counter-drills can have a variety of shapes. Thermal-setting conductive epoxies, thermal-setting conductive polyimides, solder paste, solder pre-forms, braze pre-forms and the like, are all used to make electrical connection between one or more lead wires and the associated feedthrough holes in the capacitor. Depending upon the application, these counter-drilled areas may or may not be terminated in a similar manner as the capacitor inside diameter hole or the capacitor outside diameter or perimeter.

The novel counter-drill structure of the present invention offers a number of advantages for placement of these electric-conducting materials. The counter-drill recess allows for sufficient volume of said conductive materials to be dispensed in one pass. This can be done with a hand syringe or more desirably, by a robotic dispenser. Because the counter-drill area provides for a greater volume, this will allow for robotic dispensing, for example, of thermal-setting conductive adhesives. Because of the relatively large mass of said material that is placed, typically only one centrifuging operation would be required to drive the electrical conductive material down into the inside diameter of the feedthrough capacitor passageway or hole. Another advantage of the present invention is that the counter-drill recess allows for convenient loading of a solder or braze pre-form. During high temperature re-flow operations, the counter-drill recess holds the material in place so that it cannot flow or creep to areas that are undesirable or would lead to short circuits or other reliability issues.

In the case where the lead wire that passes through the feedthrough capacitor hole is sufficiently small, and the well is sufficiently large, then it would not be necessary to have the inside wells of the counter-drill or well metallized. That is, after centrifuging, the thermal-setting conductive material would be driven down into the annular space between the lead wire and the inside diameter of the feedthrough capacitor in such a way that said thermal-setting conductive adhesive makes an electrical connection between the metallized area and the lead wire thereby connecting the lead wire to the active electrode plate set. However, in the case where the lead wire is a relatively tight fit to the inside diameter of the feedthrough capacitor, it would be desirable to also metallize the inside diameter or inside walls of the counterbore or well so that one is assured of a continuous electrical connection between the metallization that connects all of the active electrode plates in parallel to the inside diameter or inside perimeter of the well such that the thermal-setting conductive material or solder connects all of the active electrode plate sets to the lead wire.

In another embodiment the inside diameter metallization of the feedthrough hole can be eliminated as well as the metallization on the inside diameter of the well. In this case, a sufficient space is left between the lead wire and the capacitor feedthrough hole such that a thermal-setting conductive material can be centrifuged into place. As previously mentioned, the well would contain a sufficient volume of the thermal-setting conductive material that after centrifuging, it will be driven into by centrifugal force and substantially fill in the angular space between the lead wire in the inside diameter of the feedthrough capacitor. However, in this case, the feedthrough capacitor itself has no inside diameter metallization. This is very novel in that prior art feedthrough capacitors typically have a fired or plated on metallization to be assured that proper contact is made to all of the electrode plates. One way to ensure proper contact to all the electrode plates is the centrifuging operation and driving down of sufficient material so that it makes intimate contact with the exposed end of the electrodes within the capacitor through hole. A way to further improve this process is to carefully control the shrinkage between the bulk ceramic capacitor dielectric and the electrode plates themselves. After the holes are drilled and the capacitor is sintered at high temperature, considerable shrinkage occurs. By controlling a differential shrinkage between the electrode plates and the bulk ceramic, one can cause the electrode plates to stick out into the feedthrough hole. Therefore, when the thermal-setting conductive material is centrifuged into place, it will contact and grab onto a larger surface area of the exposed electrode thereby assuring a high reliable and low impedance electrical connection.

The present invention also allows for optional slotted washers to be placed between the hermetic seal feedthrough assembly and the feedthrough capacitor. This is to allow for an air flow channel between each terminal pin to the outside diameter or perimeter. This is important, for example, during soldering operations. During a high temperature re-flow operation, any air that is trapped between the lead wire and feedthrough capacitor inside diameter tends to be expanding as heat is applied. If a solder pre-form, thermal-setting conductive material or the like is sitting on the top, it tends to be blown upward by this expanding air. This is counter balanced by the forces of gravity and capillary action as the solder tries to flow down near the plates. The result, however, usually involves voids and bubbles which are undesirable in the solder surface. The presence of air channels allows the air to escape out through the bottom as the solder nicely drops into place between the lead wire outside diameter and the feedthrough capacitor through-hole inside diameter.

This is generally not necessary when the material is to be centrifuged. When using a centrifuged or pressure injected thermal-setting conductive polyimide, it is desirable to use solid washers so that the high acceleration forces from centrifuging do not drive the material out through the bottom of the capacitor all the way to its outside diameter (or from pin to pin) where short circuits could result.

Another way to think of the novel counter-drills is that they form wells for proper material placement. As mentioned, the counter-drilled wells have a number of important purposes. One is the short term storage of sufficient material to perform reliable electrical connections in a single operation. Another important reason for having a well around each lead wire is that the placement of the electrical conducting material is very highly controlled. This increases the reliability of the completed assembly by eliminating the possibility of conductive slivers, conductive creepage or the like. When conductive particles creep into the wrong area (for example, from lead to lead or from a lead wire to ground) this can result in reduced insulation resistance, reduced battery life of the active implantable device or in the worse case, catastrophic short circuiting.

It is also possible to form any of the counter-bore, counter-drill, counter-sink or semicircular wells of the present invention by pressing these shapes into the ceramic capacitor in its green state. Green state means when the capacitor has not yet been fired so it is still relatively plastic. Then the capacitor can be subsequently fired (sintered) in order to permanently form the shapes as described.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 8 is an exploded view of the unipolar feedthrough capacitor of FIGS. 2 and 3;

FIG. 9 is an exploded view similar to FIG. 8, but of the quad-polar feedthrough capacitor of FIGS. 5 and 6;

FIG. 12 is an enlarged sectional view taken generally along the line 12-12 of FIG. 10;

FIG. 13 is an enlarged, fragmented sectional view taken of the area indicated by the line 13 in FIG. 12, illustrating a methodology of dispensing a thermal-setting conductive material with an injection syringe;

FIG. 14 is a variation of the section shown in FIG. 13 wherein the lead wire is much larger in diameter and nearly fills the feedthrough hole;

FIG. 16 is a perspective view of a feedthrough terminal assembly similar to that illustrated in FIG. 10, except that the counter-bores have been completely filled up with electrical conductive material;

FIG. 17 is a perspective view of an exemplary bonding washer disposed beneath the feedthrough capacitor in FIG. 16;

FIG. 18 is a sectional view similar to that illustrated in FIG. 12, illustrating an alternative counter-bore shape and electrical conductive material disposed therein;

FIG. 19 is an enlarged fragmented sectional view taken of the area designated by the number 19 in FIG. 18;

FIG. 20 is an enlarged fragmented sectional view showing an alternative embodiment and taken of the area indicated by the number 20 in FIG. 18;

FIG. 21 is an enlarged fragmented sectional view showing an alternative embodiment and taken of the area indicated by the number 21 in FIG. 18;

DETAILED DESCRIPTION OF THE PREFERRED EMBODIMENTS

Figure 1:
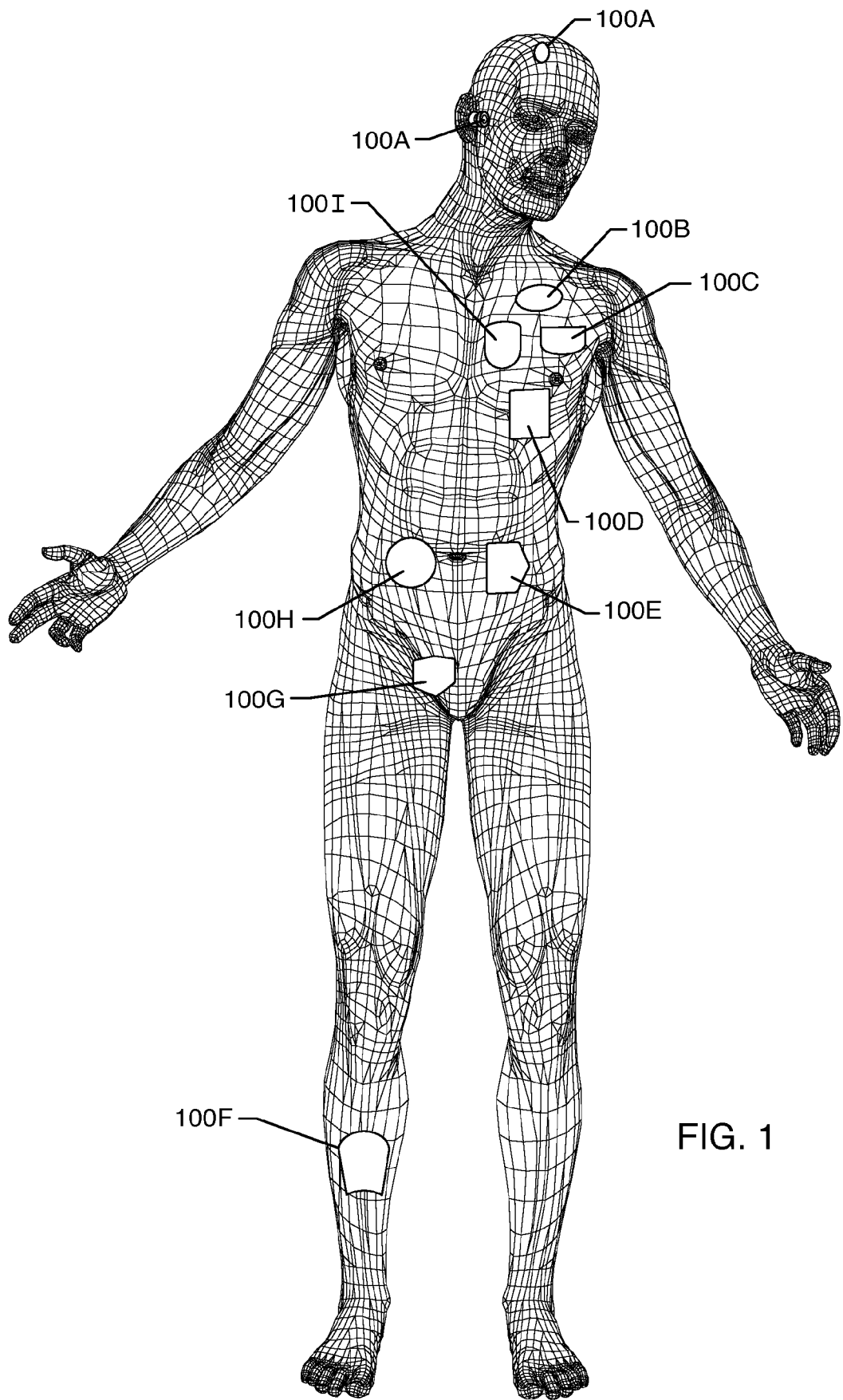
FIG. 1 is a wire-formed diagram of a generic human body illustrating placement of a number of implanted medical devices.

FIG. 1 is a wire formed diagram of a generic human body showing a number of implanted medical devices. 100A represents a family of hearing devices which can include the group of cochlear implants, piezoelectric sound bridge transducers and the like. 100B represents a variety of neurostimulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of the seizure and also providing electrical stimulation to brain tissue to prevent the seizure from actually occurring. The lead wires associated with a deep brain stimulator are often placed using real time MRI imaging. Most commonly such lead wires are placed during real time MRI. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of bone growth stimulators for rapid healing of fractures. 100G includes urinary incontinence devices. 100H includes the family of pain relief spinal cord stimulators and antitremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices.

Figure 2:
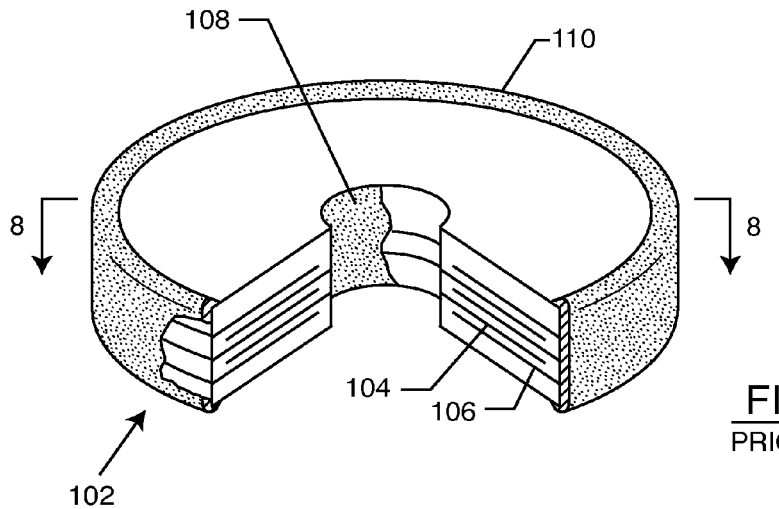
FIG. 2 is a partially fragmented perspective view of a prior art unipolar discoidal feedthrough capacitor.

FIG. 2 is a prior art unipolar discoidal feedthrough capacitor 102. The capacitor 102 includes an active internal electrode plate set 104, a ground electrode plate set 106, an inside diameter termination surface 108 which is connected electrically to the active electrode plate set 104, and an outside diameter termination surface 110 which is both solderable and electrically conductive, which is connected to the outside diameter (ground) electrode plate set 106.

Figure 3:
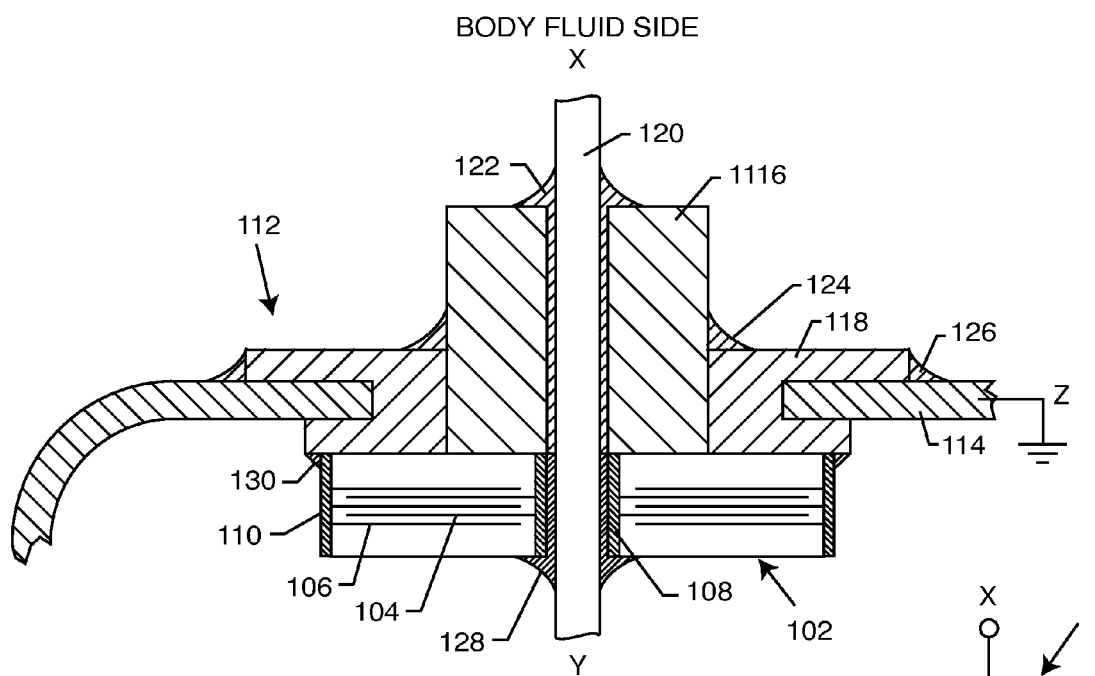
FIG. 3 is a cross-sectional view of the unipolar feedthrough capacitor of FIG. 2 shown mounted to a hermetic terminal of an active implantable medical device (AIMD)

FIG. 3 is a cross-section of the unipolar feedthrough capacitor 102 of FIG. 2 shown mounted to a hermetic terminal 112 of an active implantable medical device (AIMD). The hermetic terminal 112 is attached to, typically, a titanium housing 114, for example, of a cardiac pacemaker. An insulator 116, like alumina ceramic or glass, is disposed within the ferrule 118 and forms a hermetic seal against body fluids. A continuous terminal pin or lead wire 120 extends through the hermetic terminal 112, passing through aligned passageways through the insulator 116 and the capacitor 102. A gold braze 122 forms a hermetic seal joint between the terminal pin 120 and the insulator 116. Another gold braze 124 forms a hermetic seal joint between the alumina insulator 116 and the titanium ferrule 118. A laser weld 126 provides a hermetic seal joint between the ferrule 118 and the active implantable medical device (AIMD) housing 114. The feedthrough capacitor 102 is shown surface mounted in accordance with U.S. Pat. No. 5,333,095, the contents of which are incorporated herein, and has an electrical connection 128 between its inside diameter metallization 108 and hence the active electrode plate set 104 and lead wire 120. There is also an outside diameter electrical connection 130 which connects the capacitor's outside diameter metallization 110 and hence the ground electrodes 106 to the ferrule 118. Feedthrough capacitors are very efficient high frequency devices that have minimal series inductance. This allows them to operate as EMI low-pass filters over very broad frequency ranges.

Figure 4:
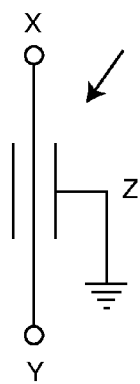
FIG. 4 is an electrical schematic diagram of the feedthrough capacitor of FIGS. 2 and 3.

FIG. 4 is a schematic diagram showing the unipolar feedthrough capacitor previously described in FIGS. 2 and 3.

In the description that follows, functionally equivalent components have the same reference numbers.

Figure 5:
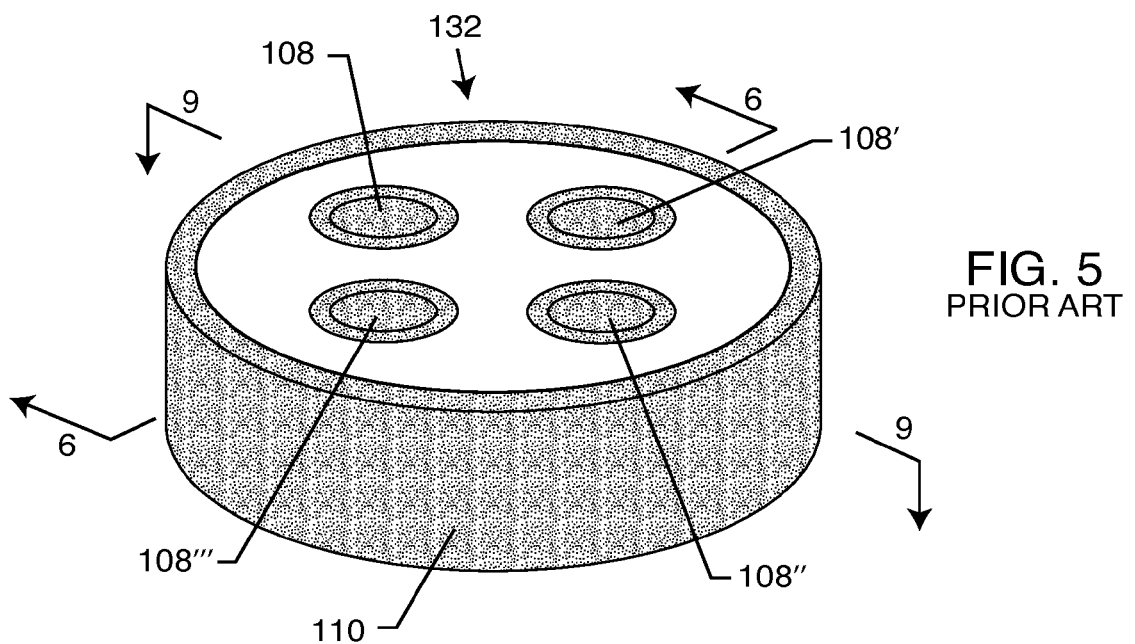
FIG. 5 is a perspective view of a prior art quad-polar feedthrough capacitor.

FIG. 5 is a prior art quadpolar feedthrough capacitor 132, which is similar in construction to that previously described in FIG. 2 except that it has four through holes.

Figure 6:
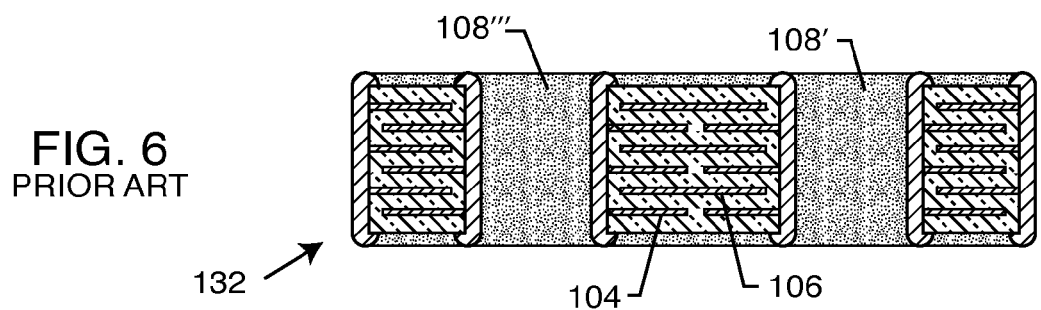
FIG. 6 is a sectional view taken generally along the line 6-6 of FIG. 5.

FIG. 6 is a cross-section showing the internal electrodes 104 and 106 of the quadpolar capacitor 132 of FIG. 5.

Figure 7:
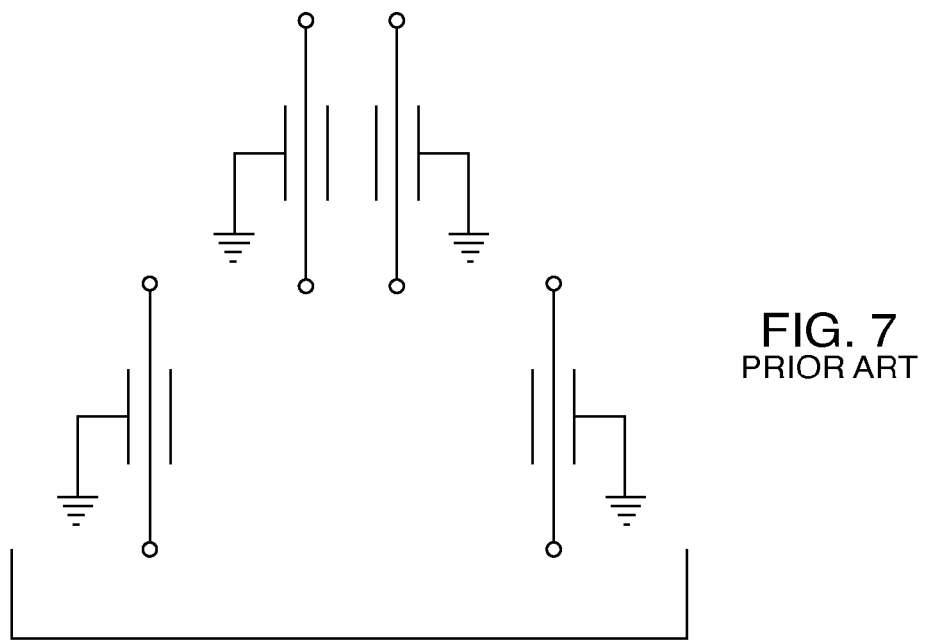
FIG. 7 is an electrical schematic diagram of the quad-polar feedthrough capacitor of FIGS. 5 and 6.

FIG. 7 is a schematic diagram showing the four feedthrough capacitors of the quadpolar feedthrough capacitor 132 of FIGS. 5 and 6.

FIG. 8 is an exploded electrode view showing the inner (active) and outer diameter (ground) electrodes of the unipolar feedthrough capacitor 102 of FIGS. 2 and 3. Here one can see the active electrode plates set 104 and the ground electrode plate set 106. Cover layers 134 are put on the top and bottom for added electrical insulation and mechanical strength.

FIG. 9 is an exploded view of the interior electrodes of the prior art quadpolar feedthrough capacitor 132 previously illustrated in FIG. 5. The active electrode plate sets 104, the ground electrode plates sets 106, and the cover sheets 134 serve the same purposes as previously described.

Figures 10, 11:
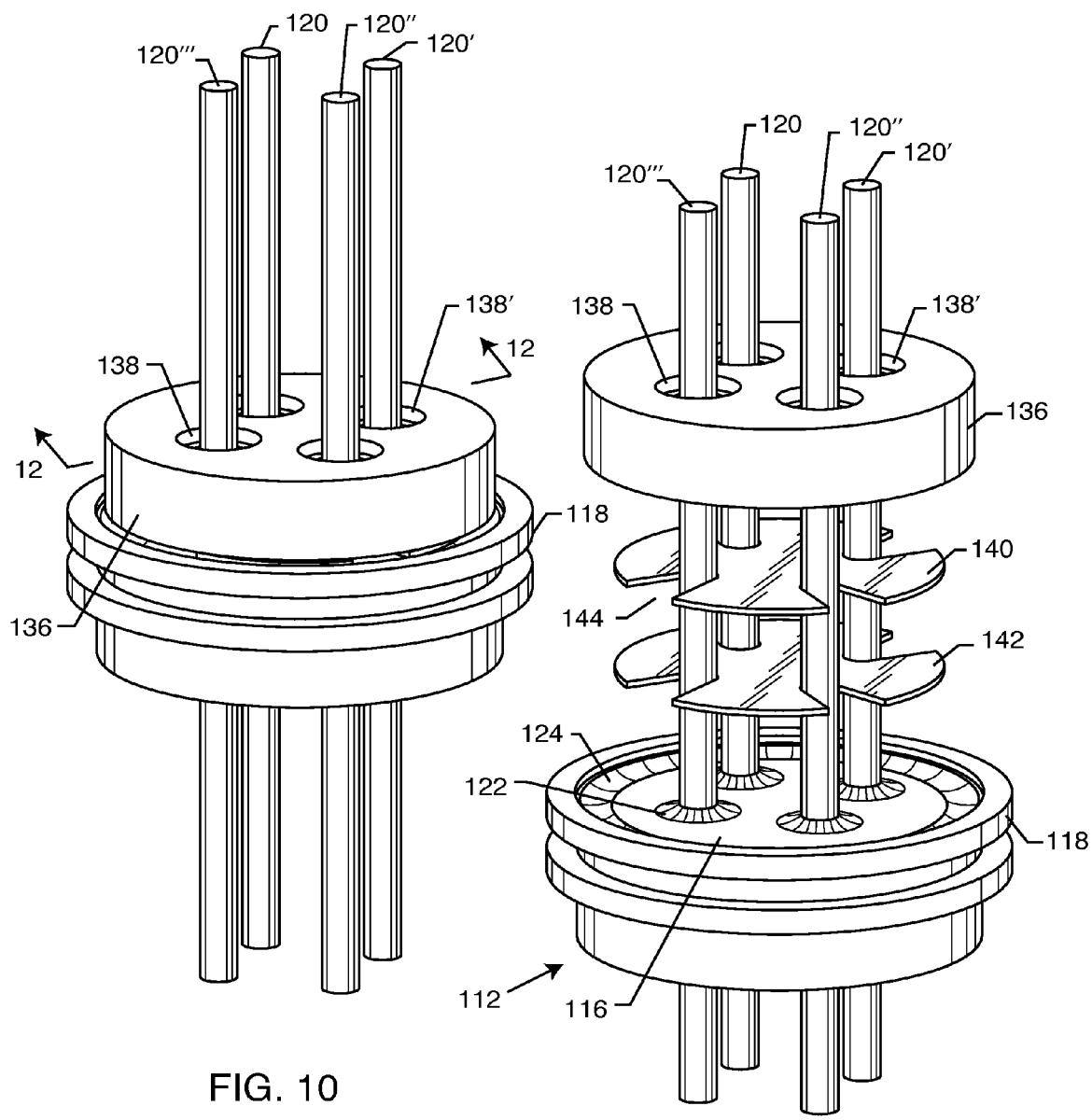
FIG. 10 is a perspective view of a quad-polar feedthrough capacitor mounted to a hermetic terminal ferrule, the quad-polar feedthrough capacitor including counter-bores in accordance with the present invention.
FIG. 11 is an exploded perspective view of the assembly shown in FIG. 10.

FIG. 10 shows a quadpolar feedthrough capacitor 136 mounted to a hermetic terminal ferrule 118. As previously described in FIG. 3, this ferrule 118 is generally made of titanium and is suitable for laser welding to the housing of the implantable medical device, such as cardiac pacemaker or the like. The feedthrough capacitor 136 illustrated in FIG. 10 is very similar to the prior art quadpolar feedthrough capacitor 132 shown in FIGS. 5, 6 and 9.

The primary novel feature is that a well 138 has been formed around each one of the lead wires 120. This well 138 forms a very convenient structure for containment of a solder pre-form, solder paste, braze material, thermal-setting conductive adhesive or the like.

It is a problem in prior art assemblies, such as those described in FIG. 3, to properly place electric conductive material 128. For example, when this is a thermal-setting conductive polyimide, a manual or robotic syringe is used to dispense this liquid or paste (semi-liquid) material. Then, in the prior art, centrifuging operations are used to dispose the material 128 properly down into the inside diameter termination area 108 of the capacitor. This usually involves an interactive process with the necessity to repeat these steps several times. This is not only time consuming, but also results in lower process yields. Referring once again to the novel structure shown in FIG. 10, the well 138 solves all the aforementioned problems. In addition to containment of the electric conducting materials, it also allows for sufficient volume of said materials to be dispensed in one pass. Because it provides for greater volume, this will allow for robotic type dispensing, for example, of thermal-setting conductive adhesives. In addition, because of the relatively large mass of such materials, typically none or only one centrifuging operation would be required to drive the electrical conductive material (128) into the inside diameter of the feedthrough capacitor 136. Another advantage of the present invention is this allows a solder pre-form to be placed into the well 138 without the necessity to crimp it to one of the lead wires 120.

FIG. 11 is an exploded view of the hermetic terminal shown in FIG. 10. Two novel washers 140 and 142 are illustrated. These washers would typically be of an adhesive-backed polyimide or the like. It will be obvious to those skilled in the art that non-adhesive washers along with liquid epoxies could be used and are completely equivalent. The washers 140 and 142 could be adhesive-backed, adhesive coated, adhesive sprayed, adhesive printed or equivalent. The washers 140 and 142 each have four openings 144. This provides an air path between the inside diameter of the capacitor and its outside diameter. This is important when the electrical conductive material (128) that is going to be placed into well 138 is of a solder, conductive glass or braze material. The reason for this is during high temperature operations, the air that is entrapped between the lead wire 120 and the capacitor inside diameter expands. This outrushing of entrapped air can lead to pin holes or failure of the solder to drop down into the inside diameter annular space of the feedthrough capacitor. The presence of the air passage 144 allows this air to escape and therefore allows the solder to properly drop and flow into the space between the lead wire and the capacitor inside diameter. In the case where the electrical conductive material to be placed in the well 138 is a thermal-setting conductive adhesive, such as a conductive polyimide, then the gap 144 and slotted washers 140 and 142 would not be required. In fact it would be undesirable. The reason for this is that when the thermal-setting conductive material is centrifuged, it would tend to flow out through gap 144 which would be very undesirable and possibly create short circuits.

Referring once again to FIG. 11, the adhesive that is used in combination with washers 140 and 142 can be either thermal-setting insulative material or thermal plastic. The purpose of this adhesive is to first of all bond the feedthrough capacitor 136 to the hermetic terminal assembly 112 consisting of flange ferrule 118, ceramic insulator 116 and its associated hermetic brazes 122 and 124.

FIG. 12 is a cross-sectional view taken generally from section 12-12 from FIG. 10. Here, one can see the novel wells 138 and 138' of the present invention. Electrical conductive material 128 is shown in its proper location. On the left side of FIG. 12, conductive material 128 can be either a solder, thermal-setting conductive adhesive or the like, as previously described. In this case, it has either been centrifuged and then cured, or the solder has flowed down into the proper location. It should be noted, in this case, some excess material 128' is left up into the well itself. On the right hand side an alternative is shown whereas after extensive microblasting (cleaning), for example, the conductive material 128 is now flush with the bottom of the well 138'.

FIG. 13 illustrates the methodology of dispensing a thermal-setting conductive material 128 with an injection syringe 146. It will be obvious to those skilled in the art that this could be manually dispensed by a human, but would be typically controlled by an automated dispensing robot. After the well 138 is filled, then the material can either be flowed or centrifuged into place as shown in well 138' of FIG. 12.

FIG. 14 is a variation of the section shown in FIG. 13. In this case, the lead wire 120''' is much larger in diameter and nearly fills the feedthrough hole. Also, there is an inside diameter metallization 108' that is applied to the inside diameter of the capacitor feedthrough hole and the inside diameter of the well. In this case, the electrical conductive material 128 is dispensed into the well. Centrifuging may be done, but is not required. This is because the electrical connecting material makes contact between the lead wire 120''' and the inside diameter metallization of the well 108'. Since the inside diameter metallization of the well 108' is contiguous with the inside diameter metallization of the feedthrough capacitor 108, this has the effect of electrically connecting the lead wire 120''' to the active electrode plate set in accordance with the present invention.

Figure 15:
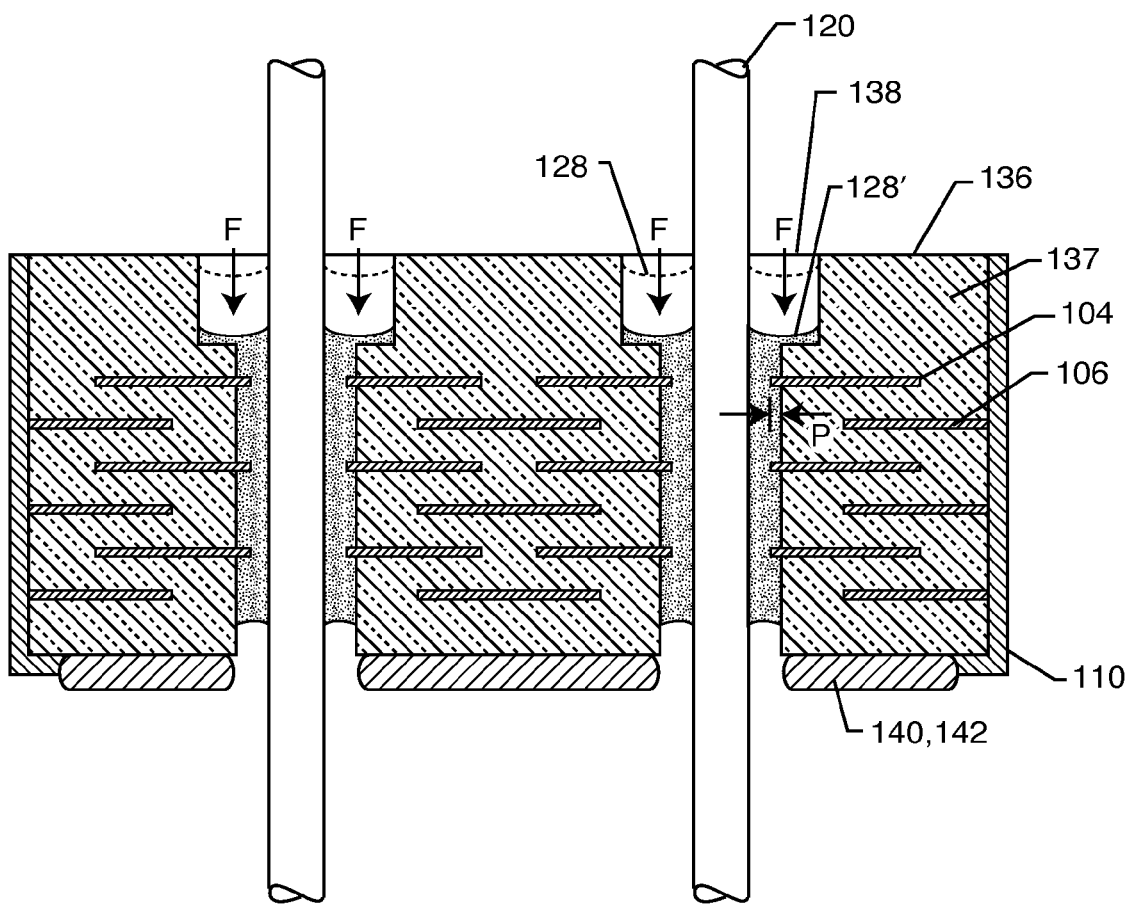
FIG. 15 is a sectional view similar to FIG. 12, except that the capacitor inside diameter metallization has been completely eliminated.

FIG. 15 is very similar to FIG. 12 except that the capacitor inside diameter metallization 108' has been completely eliminated. There is also no need for metallization on the inside diameter of the well 138. In FIG. 15, one can see that the active electrodes 104 make direct contact with a thermal-setting conductive polymer 128'. A syringe dispenser is first used to dispense the thermal-setting polymer to fill the well 138 to the approximate level of 128. Then during centrifuging, centrifugal forces F are applied to the material 128 so it settles down into location 128'. This has the effect of causing the material 128' to solidly pack into the area around the excursion of the electrode plates 104. In contrast, the outside diameter electrode plates, in a preferred embodiment, are connected to an outside diameter metallization 110. Referring once again to the inside diameter, the contact between a thermal-setting conductive epoxy electrical connection material 128' and the active electrode plate set 104, can be further improved by controlling the thermal shrinkage and the rheology between the bulk ceramic 137 and the electrode plates 104 themselves. This can be done by variations in solvent and metal loading between the bulk dielectric 137, in its green state, and the electrode plates 104. First, the feedthrough capacitor through hole is drilled and then the ceramic capacitor is sintered (fired) at very high temperature. This makes it into a hard monolithic ceramic block. Having the bulk dielectric 137 shrink in a linear direction during sintering more than the electrode 104 causes the electrode 104 to protrude out into the inside diameter area. This protrusion space is noted as P. In this way, the electrically thermal-setting conductive material 128 makes contact not only at the end of the electrode plates 104, but also along the edges around the protruding part of the electrode thereby reducing the contact resistance and improving the reliability of the connection. The protruding part of the electrode P can be further enhanced by a process of acid-etching. With the right solution of acid, one can cause the barium titinate or dielectric material 137 to be selectively etched while leaving the electrode 104 intact. This has the effect of causing the electrode protrusion P into the capacitor through-hole space to be increased.

Elimination of the capacitor inside diameter termination reduces a number of process steps and greatly reduces the cost of the overall assembly. In an alternative embodiment (not shown), outside diameter metallization could also be eliminated and the ground electrode plates could also protrude around the outside diameter of the capacitor. In this case, the outside diameter of the capacitor would also be put into a well and/or the thermal-setting conductive material would have to be placed up along the side such that the ground electrode plates 106 all ended up electrically in parallel.

FIG. 16 is very similar to FIG. 10 except that the wells 138 have been completely filled up with the electrical conductive material 128. Alternatively, one could first dispense the electrical conductive material 128 and then place over it a non-conductive thermal-setting polymer so that an insulative cap was formed. This has a number of advantages in that it increases the insulation resistance from pin to pin and pin to ground. It also provides mechanical strength during lead wire 120 bending and a nice finished cosmetic appearance. Accordingly, in the present invention, the wells 138 can either be partially filled or totally filled with the conductive material 128 or they can be partially filled with a conductive material and then topped off with a suitable non-conductive filler (such as a non-conductive epoxy). In this case, the bonding washer 150 underneath the feedthrough capacitor 136 is of a solid shape as illustrated in FIG. 17. This means that the electrical conducting material 128 would be a thermal-setting conductive polymer suitable for centrifuging into place.

FIG. 18 is very similar to FIG. 12 in that it contains wells 138 of the present invention. The left hand well 138 would typically be known in the art as a counter-bore. This would typically be formed by a two-flute flat bottomed end mill. This is typically done with automated drilling machines that are presently used to make conventional feedthrough capacitors. These automated drilling machines are capable of picking up a variety of tools or a variety of bits as needed. Because of the abrasive nature of the ceramic material feedthrough 136, such bits or tools are typically carbide or carbide coated so that they become more resistant to abrasion.

On the right hand side of FIG. 18 is shown well 138' which is formed in a counter-sink shape. There are some advantages to the counter-sink in that it is easier to form using conventional drills of a larger diameter. In this case, it is the tip of the drill that forms the counter-sink which is typically at an angle of 118 degrees. Custom drills could be used to create other angles as needed.

FIG. 19 is a close up of the counter-bore 138 previously described in the left-hand side of FIG. 18, prior to re-flow of solder preform or equivalent material 128.

FIG. 20 is a close up of counter-sink 138' previously described in the right side of FIG. 18.

FIG. 21 is yet another embodiment of a well 138' that forms a semi-circular shape. This well 138' would typically be formed by the tip of a ball end mill. The counter-sink and semi-circular ball end mill shapes illustrated in FIGS. 20 and 21 are particularly ideal for the wetting of electrical conductive materials 128 and their dispensing and subsequent flow or placement between the lead wire and the capacitor inside diameter. Any variety of other shapes that are similar to those illustrated to FIGS. 19, 20 and 21 could also be employed. Accordingly, the wells 138 of the present invention can be formed of any shape using any combination of tools as desired. The shapes described herein are therefore for a preferred embodiment illustrative purposed only and do not limit the present invention or scope. Such variations, for example in FIG. 19, could be tilting the sides of the well 138 so they form an angle with a flat bottom or even a curved or a radius bottom. The counter-sink as previously mentioned in FIG. 20 could be of any particular angle or it could even be of a variety of curve shapes. The semi-circular shape shown in FIG. 21 could be elliptical or any other shape that could be imagined. Or it could be a combination of any of the aforementioned figures or shapes.

Figure 22:
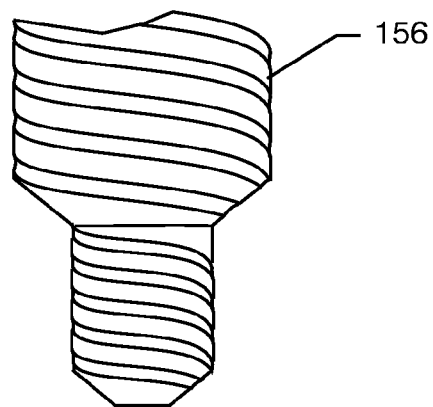
FIG. 22 is a fragmented, perspective view of an exemplary drill bit for forming a counter-sink shape.
Figure 23:
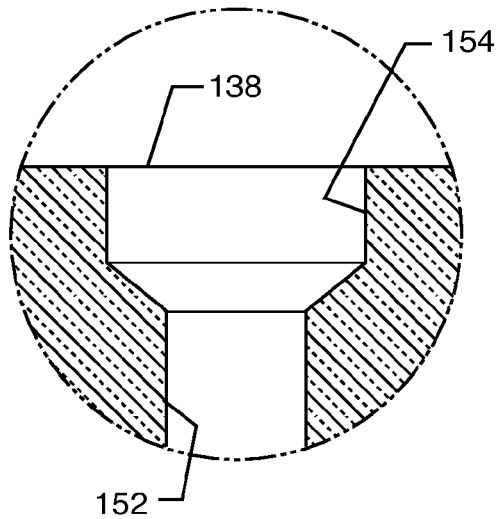
FIG. 23 is an enlarged fragmented perspective sectional view of the area indicated by the number 19 in FIG. 18, showing the counter-bore formed by the drill of FIG. 22.
Figure 24:
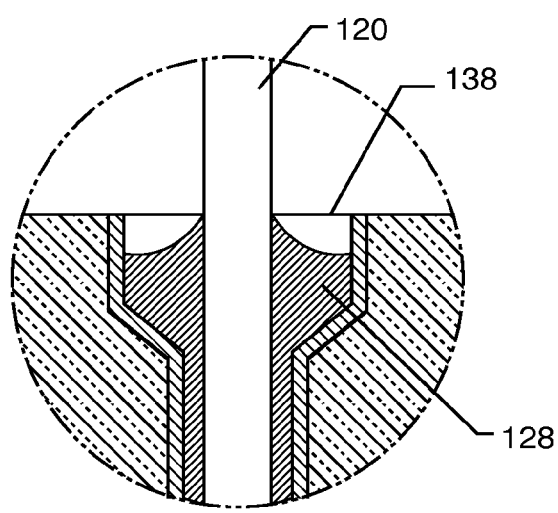
FIG. 24 is a view similar to FIG. 23, illustrating attachment of a lead wire within the formed counter-bore.

One useful combination is a combination of a counter-sink and a counter bore. This is typically performed by first drilling the straight through hole and then coming in with a larger diameter bit which forms straight sides and a counter sunk bottom automatically. This is best illustrated by looking at FIGS. 22, 23 and 24. First, a straight through-hole 152 is drilled, and then a larger drill hole 154 as shown in FIG. 23 is used to drill out a counter-sink shape. This forms the composite well 138 as illustrated. This of course, could also be done with a special type of drill known as a composite drill 156 as shown in FIG. 22, wherein the smaller through-hole portion of the drill was contained below the larger portion of the drill so that this could all be done in a single drilling/boring operation.

The formation of the feedthrough holes and the novel wells of the present invention are easily performed by robotic operations. That is, it has become very common in the manufacturing of feedthrough capacitors to drill their center holes using automated printed circuit board drilling machines. Bars of green ceramic material are typically placed inside the robotic drilling machine. These bars already contain the inner and outer electrode patterns and have been laminated. Tens or even hundreds of capacitors are in one single bar. Automatic pattern recognition programs are used. The automated drilling machine automatically picks up the right bit size, automatically locates the center of each hole and drills it very quickly. This is done much more accurately than can be done by the human eye. These same printed circuit board automated drilling machines also have the capability of automatically picking up other bits. Therefore, for very little additional labor expense, the machine can be programmed to pick up the various tool shapes to form the various wells (counter-sinks, counterbores, etc.) of the present invention.

Figure 25:
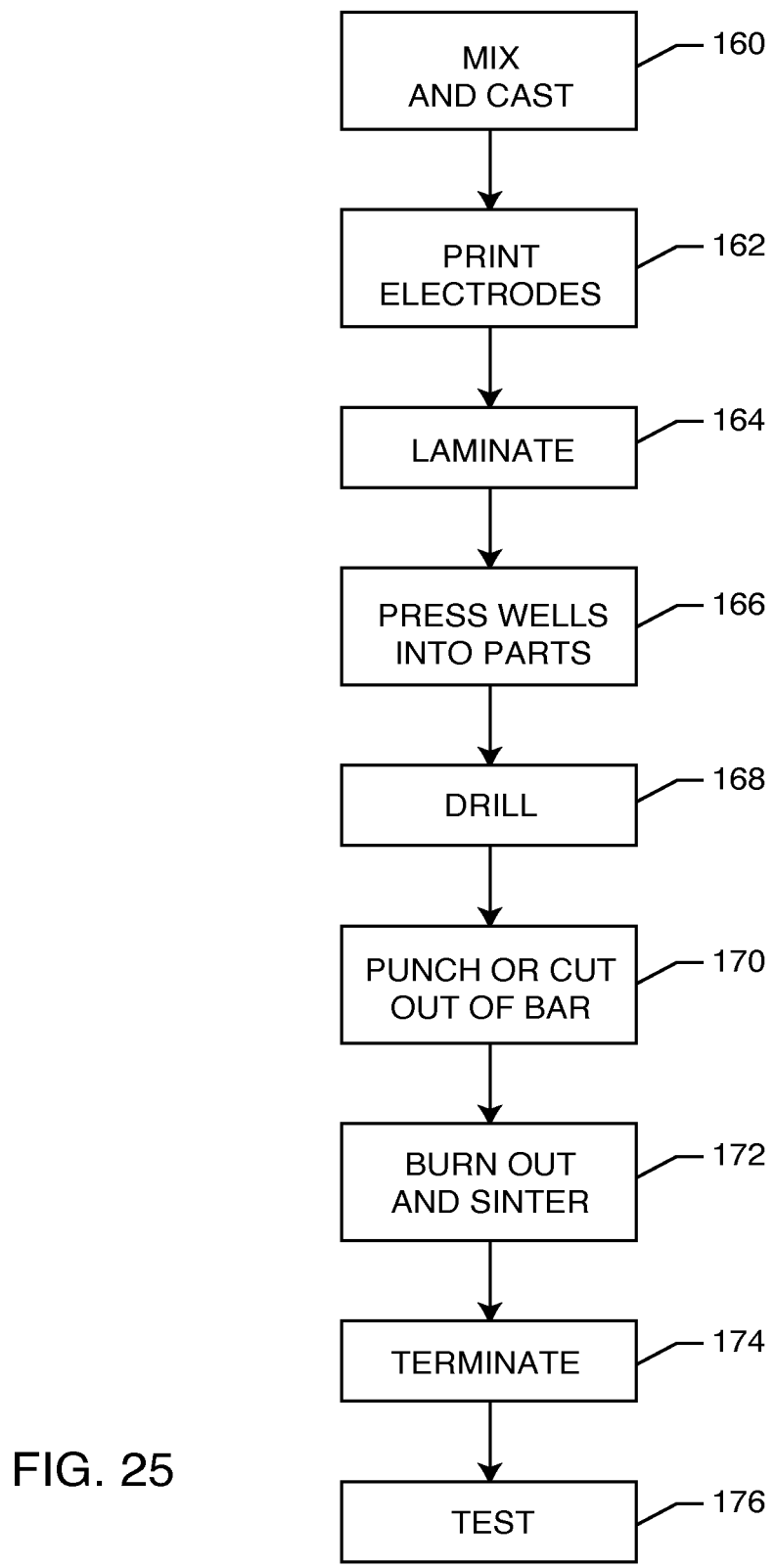
FIG. 25 is a flow chart illustrating a process for forming counter-bores in a green-state capacitor.
Figure 26:
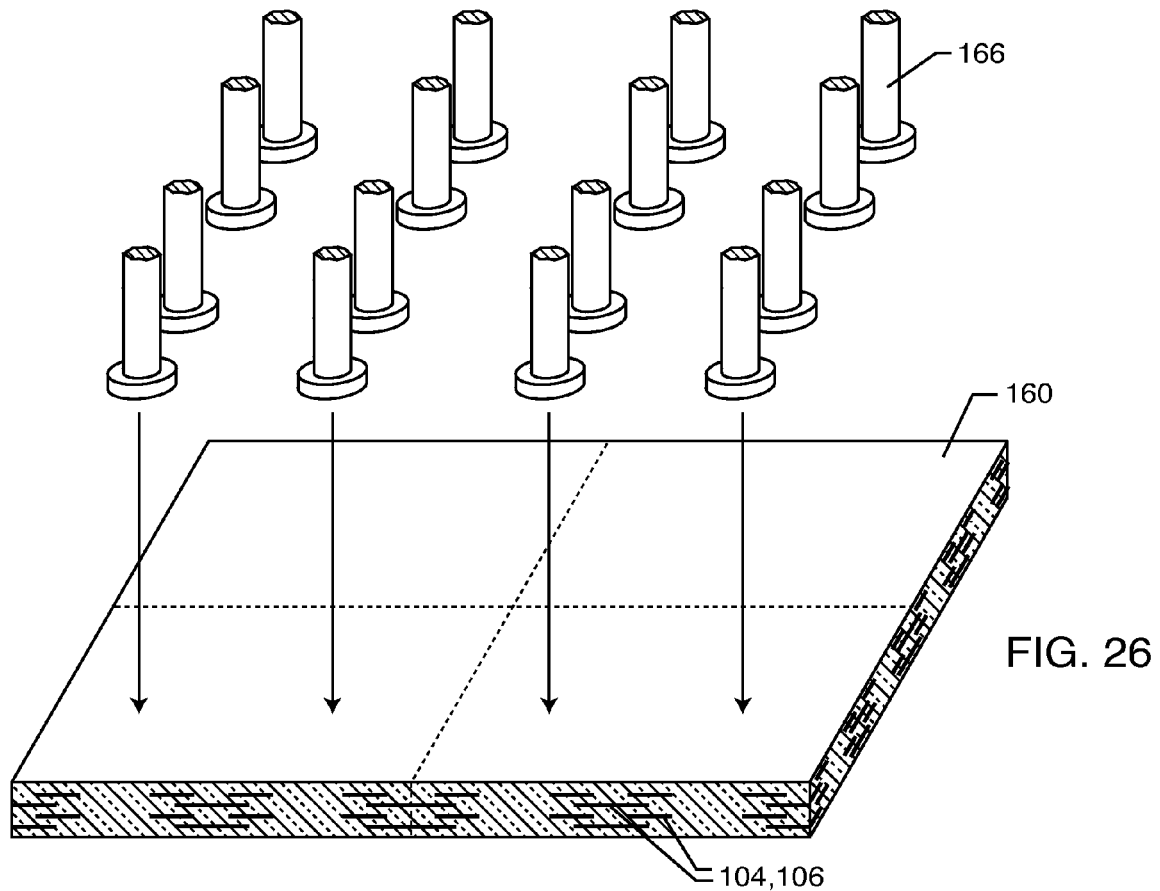
FIGS. 26-31 further illustrate the process steps shown in the flow chart of FIG. 25.
Figure 27:
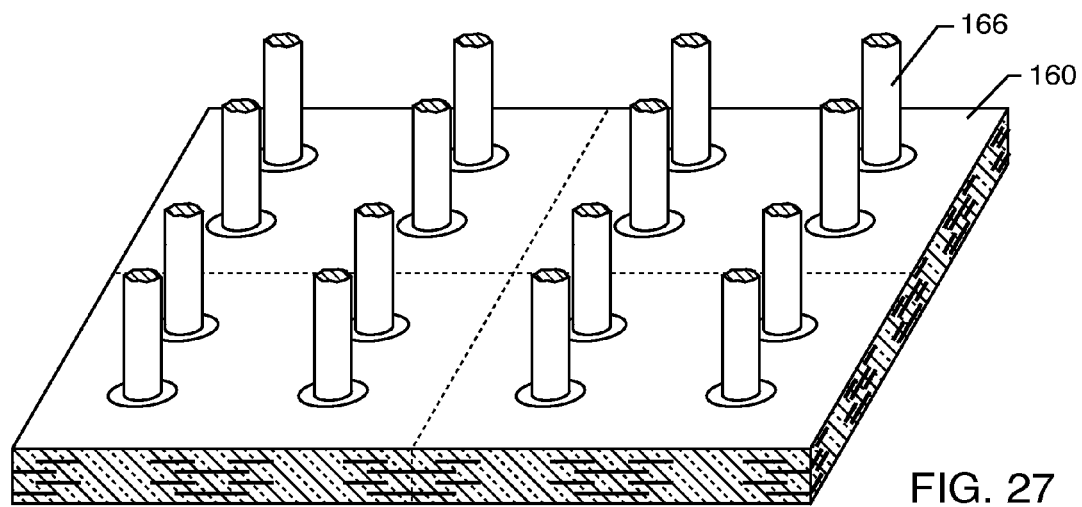
Figure 28:
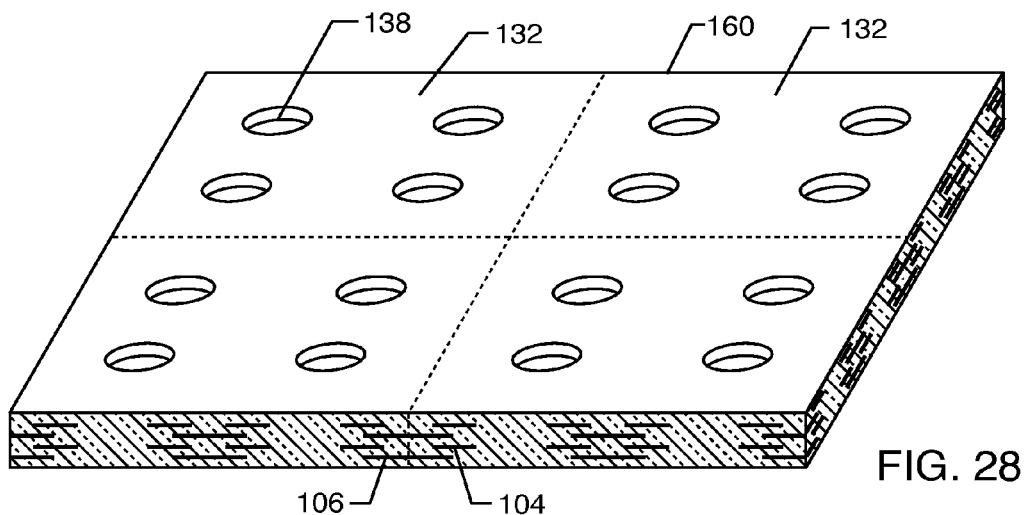
Figure 29:
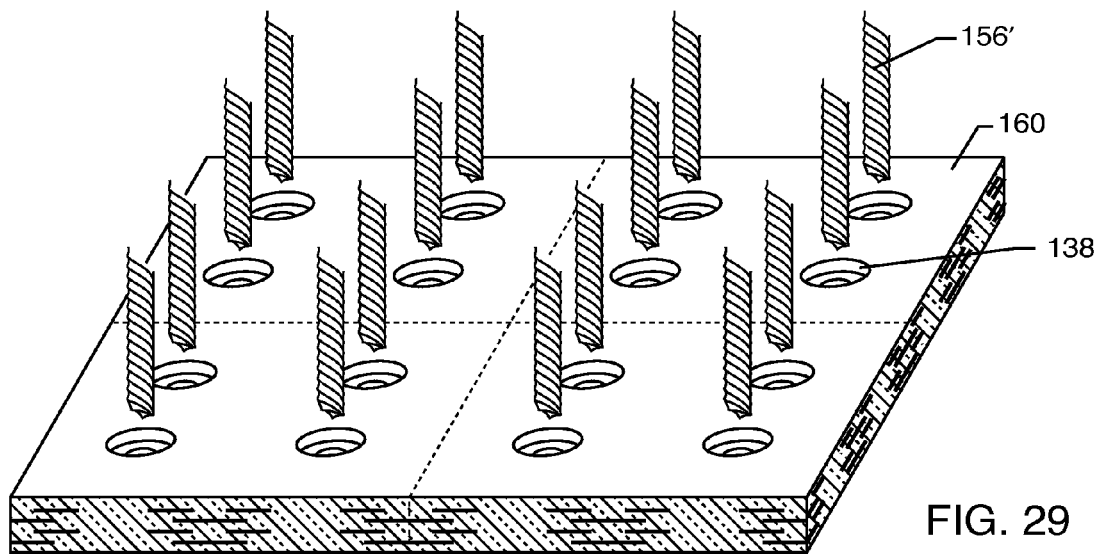
Figure 30:
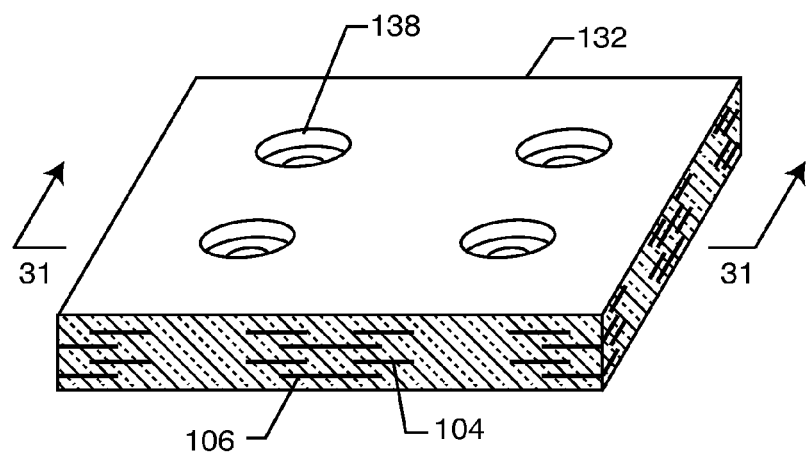
Figure 31:
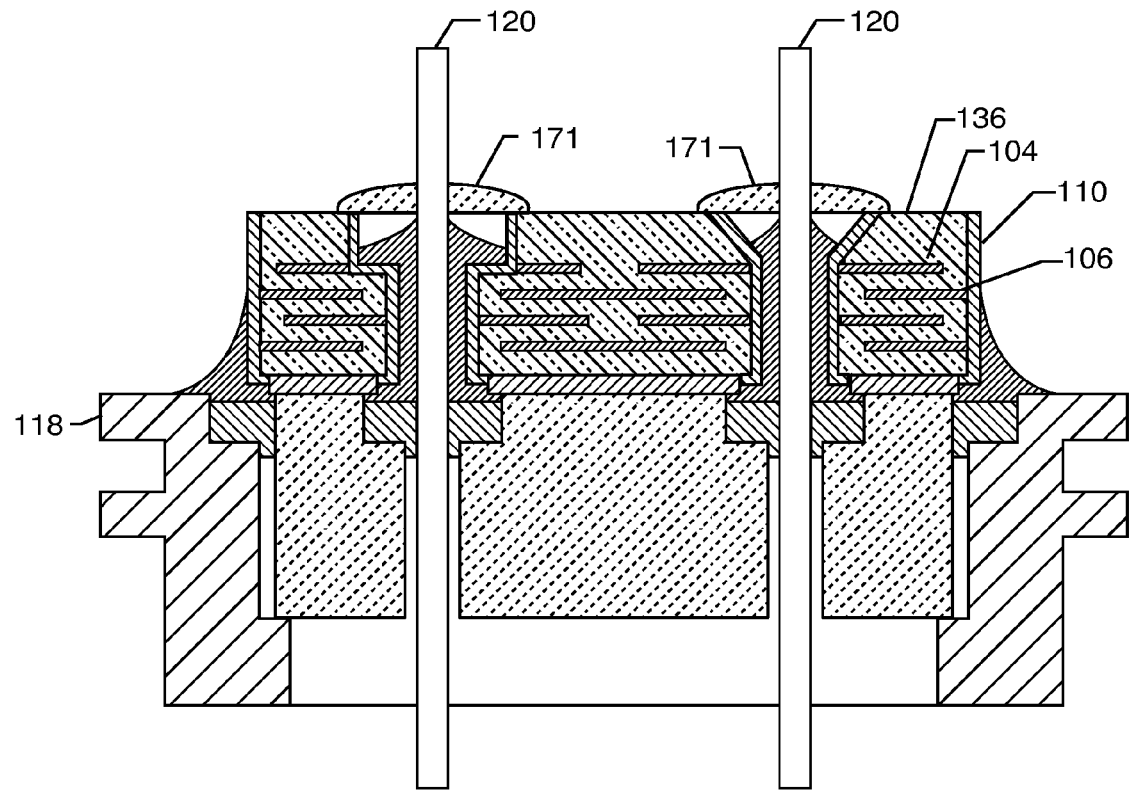

FIG. 25 is a flow chart showing a novel way to form the wells 138 of the present invention with the capacitor in the green state. First the ceramic dielectric slurry is mixed and cast into a thin flexible film (160) as shown in FIG. 26. Electrodes 104, 106 are embedded into the bar 160 as shown in FIG. 26. The wafer size can vary from small to large depending upon the manufacturing processes. These printed electrode sheets are stacked up to form the number of layers of the ceramic feedthrough capacitors. The bar 160 as shown in FIG. 26, has been pressed and laminated typically at high pressure and with heat. Then the wells of the present invention are cut or pressed into the green ceramic using various mating tools (166) as shown in FIG. 26 and shown during the cutting operation in FIG. 27. After the cutting or pressing operation, the bar as illustrated in FIG. 28 is shown with the wells 138 already formed. Then the entire green capacitor wafer, which is still in a sheet (in other words, the individual capacitors have not yet been punched out of the overall wafer) is put through a drilling operation (168) as shown in FIG. 29. This is followed by a punching operation 170 which punches out each individual capacitor as shown as a quadpolar capacitor in FIG. 30. The quadpolar capacitor of FIG. 30 is shown in cross-section mounted to a hermetic terminal as illustrated in FIG. 31 in accordance with the present invention. Referring to FIG. 31, a cosmetic cap of non-conductive epoxy has been added over each lead wire. This cap is used for cosmetics and also to strengthen the lead wires 20 against bending or pulling. As mentioned, the punching operation cuts the individual capacitors out of the bar. Then the capacitor will go through typical prior art burn-out and sintering process (172). Then the capacitors have both outside diameter and inside diameter terminations applied and fired (174). The final step is electrical testing (176).

Accordingly, it is a feature of the present invention that any of the novel well shapes as previously described could be literally cut or pressed into the capacitor prior to its final sintering operation.

From the foregoing it will be appreciated that the novel manufacturing process of the present invention comprises the steps of: (1) providing a capacitor comprised of a dielectric material having active and ground electrode plates therein and at least one through hole; (2) forming a well in a surface of the capacitor at one end of the through hole; (3) inserting a pin or a lead wire at least partially into the through hole; (4) placing an electrically conductive material in the well, wherein the electrically conductive material comprises a liquid or semi-liquid material during at least some portion of the manufacturing process; and (5) utilizing the electrically conductive material to conductively couple the pin or the lead wire to one of the active or ground electrode plates. In most preferred embodiments shown herein, the novel manufacturing process further includes the step of utilizing an electrically conductive material to attach the pin or the lead wire to the capacitor.

Although several embodiments of the invention have been described in detail for purposes of illustration, various modifications of each may be made without departing from the spirit and scope of the invention. Accordingly, the invention is not to be limited, except as by the appended claims.

What is claimed is:

1. A process for manufacturing an electromagnetic interference (EMI) filter for use in an active implantable medical device (AIMD), comprising the steps of:
   a) providing a capacitor comprising a thickness extending alone a longitudinal axis between spaced apart first and second capacitor surfaces meeting a capacitor outer sidewall, wherein the capacitor is comprised of a dielectric material having interleaved, but spaced apart active and ground electrode plates therein, and at least one through hole having a first diameter perpendicular to the longitudinal axis thereof;
   b) forming a well comprising a well sidewall having a continuous semi-circular shape in cross-section along an imaginary plane aligned with the longitudinal axis of the through hole, the well sidewall extending from a second diameter at the one of the first and second capacitor surfaces part-way into the thickness of the capacitor to the through hole, wherein the second diameter is greater than the first diameter of the through hole;
   c) inserting a pin or a lead wire at least partially into the well and the through hole;
   d) placing an electrically conductive material in the well, wherein the electrically conductive material comprises a liquid or semi-liquid material during at least a portion of the manufacturing process; and
   e) utilizing the electrically conductive material to conductively couple the pin or the lead wire to one of the active or ground electrode plates.

2. The process of claim 1, including selecting the electrically conductive material from the group consisting of a thermal-setting conductive adhesive, a solder, a solder preform, a solder paste, and a brazed preform.

3. The process of claim 2 the step of placing the electrically conductive material in the well includes dispensing the electrically conductive material into the well by means of a hand held syringe, a robotic syringe, robotic placement of a solder preform or hand placement of a solder preform.

4. The process of claim 1 including providing the through hole comprising a conductive termination surface conductively coupled to one of the active or ground electrode plates.

5. The of claim 4 including providing the well comprising a termination surface extending contiguously from the through hole conductive termination surface.

6. The process of claim 1 including providing the well comprising a conductive termination surface.

7. The process of claim 1 including providing the electrically conductive material conductively coupling the pin or the lead wire to one of the active or ground electrode plates directly and without an intervening conductive termination surface for the electrode plates.

8. The process of claim 7 including providing shrinkage of the dielectric material of the capacitor being greater than shrinkage of the electrode plates such that a protruding end of the electrode plates, conductively coupled to the electrically conductive material, extends inwardly from the dielectric material into the through hole.

9. The process of claim 7, including acid-etching the dielectric material adjoining the through hole prior to utilizing the electrically conductive material to conductively couple the pin or the lead wire to one of the active or ground electrode plates.

10. The process of claim 1, including the step of causing at least a portion of the electrically conductive material to flow from the well into the through hole between the capacitor and the pin or the lead wire.

11. The process of claim 10, including the step of centrifuging the electrically conductive material into the through hole.

12. The process of claim 1 including providing the capacitor comprising a plurality of through holes and a corresponding plurality of wells that are physically and electrically isolated from one another.

13. The process of claim 1 including forming the well in the surface of the capacitor when the dielectric material is in a green state.

14. The process of claim 13, including the steps of:
   a) forming a laminate structure of the active and ground electrode plates and green dielectric material of a size to create a plurality of capacitors;
   b) forming the through holes for each capacitor in the laminate structure;
   c) forming a well in connection with each of the through holes;
   d) cutting or punching the capacitors from the laminate structure; and
   e) curing the capacitors.

15. The process of claim 13 including pressing or cutting the well into the green ceramic material.

16. The process of claim 13 including first drilling the through hole followed by forming the well by drilling a larger diameter semi-circular counterbore at one of the first and second capacitor surfaces.

17. The process of claim 16 including simultaneously forming the through hole and the well using a single drilling/boring operation.

18. The process of claim 1, including the step of inserting a non-conductive material into the well and over the electrically conductive material.

19. The process of claim 1 including inserting a sufficient quantity of an electrically conductive material into the well so that space between the capacitor and the lead wire or the pin is at least partially filled with the electrically conductive material in both the well and the through hole.

20. The process of claim 1, including the step of placing a bonding washer between the capacitor and a capacitor mounting surface.

21. The process of claim 20 including providing the bonding washer having an open-ended notch configured to receive the pin or lead wire therethrough, thereby forming a path for gas to escape from the through hole as the electrically conductive material flows therein.

22. The process of claim 20, including the step of placing a plurality of bonding washers between the capacitor and the mounting surface, the bonding washers having apertures that cooperatively form a gas escape path from the through hole as electrically conductive material, flows therein.

23. The process of claim 1 including providing the active and ground electrode plates being only disposed laterally of the through hole, but not the well.

24. A process for manufacturing an electromagnetic interference (EMI) filter for use in an active implantable medical device (AIMD), comprising the steps of:
   a) providing a capacitor comprising a thickness extending along a longitudinal axis between spaced apart first and second capacitor surfaces meeting a capacitor outer sidewall, wherein the capacitor is comprised of a dielectric material having interleaved, but spaced apart active and ground electrode plates therein, and at least one through hole having a first diameter perpendicular to the longitudinal axis thereof;
   b) forming a well comprising a well sidewall having a continuous semi-circular shape in cross-section along an imaginary plane aligned with the longitudinal axis of the through hole in the capacitor to thereby provide a second diameter greater than the first diameter of the through hole extending from one of the first and second capacitor surfaces part way into the thickness of the capacitor where the well meets the through hole;
   c) inserting a pin or a lead wire at least partially into the well and the through hole;
   d) placing an electrically conductive material in the well, wherein the electrically conductive material comprises a liquid or semi-liquid material during at least a portion of the manufacturing process; and
   e) utilizing the electrically conductive material to directly conductively couple the pin or the lead wire to one of the active or ground electrode plates without an intervening conductive termination surface for the electrode plates.

25. The process of claim 24 including providing shrinkage of the dielectric material of the capacitor being greater than shrinkage of the electrode plates such that a protruding end of the electrode plates, conductively coupled to the electrically conductive material, extends inwardly from the dielectric material into the through hole.

26. The process of claim 24, including the step of acid-etching the dielectric material adjoining the through hole prior to the step of utilizing the electrically conductive material to conductively couple the pin or the lead wire to one of the active or ground electrode plates.

27. The process of claim 24 including providing the active and ground electrode plates being only disposed laterally of the through hole, but not the well.

28. A process for manufacturing an electromagnetic interference (EMI) filter for use in an active implantable medical device (AIMD), comprising the steps of:
   a) providing a capacitor comprised of a dielectric material having active and ground electrode plates therein, and at least one through hole;
   b) forming a well in a surface of the capacitor at one end of the through hole;
   c) inserting a pin or a lead wire at least partially into the through hole;
   d) placing a bonding washer against a mounting surface of the capacitor, wherein the bonding washer has an aperture configured to receive the pin or lead wire therethrough;
   e) placing an electrically conductive material in the well, wherein the electrically conductive material comprises a liquid or semi-liquid material during at least a portion of the manufacturing process;
   f) utilizing the electrically conductive material to conductively couple the pin or the lead wire to one of the active or ground electrode plates; and
   g) wherein the aperture of the bonding washer forms a path for gas to escape from the through hole as the electrically conductive material flows therein.

29. The process of claim 28 including providing the aperture as an open-ended notch.

30. A process for manufacturing an electromagnetic interference (EMI) filter for use in an active implantable medical device (AIMD), comprising the steps of:
   a) providing a capacitor comprising a thickness extending along a longitudinal axis between spaced apart first and second capacitor surfaces meeting a capacitor outer sidewall, wherein the capacitor is comprised of a dielectric material having interleaved, but spaced apart active and ground electrode plates therein, and at least one through hole having a first diameter perpendicular to the longitudinal axis thereof;
   b) forming a well comprising a well sidewall having an elliptical shape in cross-section along an imaginary plane aligned with the longitudinal axis of the through hole, the well sidewall extending from a second diameter at the one of the first and second capacitor surfaces part-way into the thickness of the capacitor to the through hole, wherein the elliptical cross-section of the well sidewall along the longitudinal axis is continuous from the second diameter being greater than the first diameter;
   c) inserting a pin or a lead wire at least partially into the well and the through hole;
   d) placing an electrically conductive material in the well, wherein the electrically conductive material comprises a liquid or semi-liquid material during at least a portion of the manufacturing process; and
   e) utilizing the electrically conductive material to conductively couple the pin or the lead wire to one of the active or ground electrode plates.

* * * * *

UNITED STATES PATENT AND TRADEMARK OFFICE
CERTIFICATE OF CORRECTION

PATENT NO.       : 8,468,664 B2
APPLICATION NO.  : 12/437345
DATED            : June 25, 2013
INVENTOR(S)      : Richard L. Brendel et al.

It is certified that error appears in the above-identified patent and that said Letters Patent is hereby corrected as shown below:

In the Claims

Column 13, line 47 (Claim 1, line 5) delete "alone" and insert --along--

Column 14, line 16 (Claim 5, line 1) insert --process-- between the words "The" and "of"

Column 15, line 24 (Claim 22, line 5) delete the "," after the word "material"

Signed and Sealed this
Sixth Day of May, 2014

Michelle K. Lee
*Deputy Director of the United States Patent and Trademark Office*